United States Patent
Qian

(10) Patent No.: US 11,054,743 B2
(45) Date of Patent: Jul. 6, 2021

(54) FLUORENE POLYFUNCTIONAL PHOTOINITIATOR AND PREPARATION AND USE THEREOF, AND PHOTOSENSITIVE RESIN COMPOSITION CONTAINING FLUORENE PHOTOINITIATOR AND USE THEREOF

(71) Applicants: CHANGZHOU TRONLY ADVANCED ELECTRONIC MATERIALS CO., LTD., Jiangsu (CN); CHANGZHOU TRONLY NEW ELECTRONIC MATERIALS CO., LTD., Jiangsu (CN)

(72) Inventor: Xiaochun Qian, Jiangsu (CN)

(73) Assignees: CHANGZHOU TRONLY ADVANCED ELECTRONIC MATERIALS CO., LTD., Changzhou (CN); CHANGZHOU TRONLY NEW ELECTRONIC MATERIALS CO., LTD., Changzhou (CN)

( * ) Notice: Subject to any disclaimer, the term of this patent is extended or adjusted under 35 U.S.C. 154(b) by 481 days.

(21) Appl. No.: 16/061,490

(22) PCT Filed: Sep. 28, 2016

(86) PCT No.: PCT/CN2016/100601
§ 371 (c)(1),
(2) Date: Jun. 12, 2018

(87) PCT Pub. No.: WO2017/101553
PCT Pub. Date: Jun. 22, 2017

(65) Prior Publication Data
US 2020/0264508 A1  Aug. 20, 2020

(30) Foreign Application Priority Data

Dec. 15, 2015 (CN) .......................... 201510937328.0
Apr. 6, 2016 (CN) .......................... 201610210118.6

(51) Int. Cl.
| | |
|---|---|
| *G03F 7/031* | (2006.01) |
| *C07C 45/46* | (2006.01) |
| *C07C 49/215* | (2006.01) |
| *G03F 7/039* | (2006.01) |
| *G03F 7/00* | (2006.01) |
| *G03F 7/40* | (2006.01) |

(52) U.S. Cl.
CPC .............. *G03F 7/031* (2013.01); *C07C 45/46* (2013.01); *C07C 49/215* (2013.01); *G03F 7/0007* (2013.01); *G03F 7/039* (2013.01); *G03F 7/40* (2013.01)

(58) Field of Classification Search
CPC ........ C07C 45/46; C07C 49/215; G03F 7/031
USPC .................................................... 430/281.1
See application file for complete search history.

(56) References Cited

U.S. PATENT DOCUMENTS

| | | |
|---|---|---|
| 4,374,984 A | 2/1983 | Eichler et al. |
| 4,533,670 A | 8/1985 | Robertson |
| 4,666,824 A * | 5/1987 | Messer .................... C08F 2/50 430/281.1 |
| 4,950,581 A | 8/1990 | Koike et al. |
| 5,077,402 A | 12/1991 | Desobry et al. |
| 5,527,925 A | 6/1996 | Chabrecek et al. |

(Continued)

FOREIGN PATENT DOCUMENTS

| | | |
|---|---|---|
| CN | 101724099 A | 6/2010 |
| CN | 102267887 A | 12/2011 |

(Continued)

OTHER PUBLICATIONS

J. Med. Chem. 1964, 7, 4, pp. 504-508 , Publication Date:Jul. 1, 1964 (Year: 1964).*

(Continued)

*Primary Examiner* — Cynthia Hamilton
(74) *Attorney, Agent, or Firm* — Westerman, Hattori, Daniels & Adrian, LLP

(57) ABSTRACT

This invention discloses a fluorene polyfunctional photoinitiator as represented by general formula (I), a photosensitive resin composition containing the same, the preparation of the same, and uses of the two. This compound has the advantages of simple synthesis, low cost, and good solubility, and has good application effects in photocurable compositions. Compared with conventional small molecule photoinitiators, it is not only excellent in photoinitiation activity, but also has the advantages such as low mobility, low odor, and yellowing resistance. The composition has high photosensitivity and good developability, high resolution, and excellent adaptation to a substrate, and is very suitable for producing a black matrix having high light-shielding property, a high-precision and high quality color filter and a liquid crystal display device, and can also be used in optical spacers and ribs, photoresist, wet film, dry film and so on.

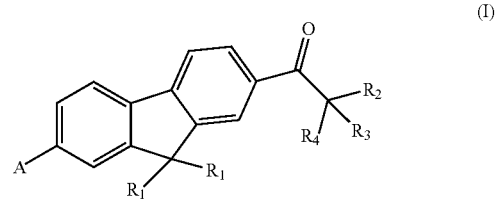

(I)

4 Claims, No Drawings

(56) References Cited

U.S. PATENT DOCUMENTS

| | | | |
|---|---|---|---|
| 5,612,389 | A | 3/1997 | Chabrecek et al. |
| 5,612,391 | A | 3/1997 | Chabrecek et al. |
| 5,621,018 | A | 4/1997 | Chabrecek et al. |
| 6,087,412 | A | 7/2000 | Chabrecek et al. |
| 6,099,122 | A | 8/2000 | Chabrecek et al. |
| 6,204,306 | B1 | 3/2001 | Chabrecek et al. |
| 6,492,514 | B1 | 12/2002 | Meneguzzo et al. |
| 9,316,906 | B2 | 4/2016 | Shin et al. |
| 9,684,238 | B2 | 6/2017 | Harihara et al. |
| 9,873,663 | B2 | 1/2018 | Oh et al. |
| 2005/0266341 | A1* | 12/2005 | Kim .................... G03F 7/0007 430/270.1 |
| 2015/0111152 | A1 | 4/2015 | Shin et al. |
| 2015/0259321 | A1 | 9/2015 | Harihara et al. |
| 2016/0046551 | A1 | 2/2016 | Shiota et al. |
| 2017/0160636 | A1 | 6/2017 | Tadokoro et al. |
| 2018/0050973 | A1 | 2/2018 | Shiota et al. |
| 2019/0155153 | A1 | 5/2019 | Qian |
| 2020/0002544 | A1* | 1/2020 | Qian .................... C07C 45/41 |

FOREIGN PATENT DOCUMENTS

| | | | |
|---|---|---|---|
| CN | 104661997 | A | 5/2015 |
| CN | 104684888 | A | 6/2015 |
| CN | 104892512 | A | 9/2015 |
| CN | 105916837 | A | 8/2016 |
| CN | 106883114 | A | 6/2017 |
| EP | 2913323 | A1 | 9/2015 |
| EP | 3165965 | A1 | 5/2017 |
| EP | 3392232 | A1 | 10/2018 |
| GB | 1189514 | A | 4/1970 |
| JP | 2001-348412 | A | 12/2001 |
| JP | 2009-19142 | A | 1/2009 |
| JP | 2009-29859 | A | 2/2009 |
| JP | 2010-024291 | A | 2/2010 |
| JP | 2017-533288 | A | 11/2017 |
| JP | 2019-528331 | A | 10/2019 |
| JP | 6725663 | B2 | 7/2020 |
| KR | 10-2014-0076607 | A | 6/2014 |
| KR | 10-2014-0144809 | A | 12/2014 |
| KR | 20140144809 | A * | 12/2014 |
| KR | 10-2015-0040372 | A | 4/2015 |
| KR | 101567837 | B1 | 11/2015 |
| KR | 10-2017-0032372 | A | 3/2017 |
| WO | 2005/014515 | A2 | 2/2005 |
| WO | 2013/165207 | A1 | 11/2013 |
| WO | 2014/050738 | A1 | 4/2014 |
| WO | 2015/084114 | A1 | 6/2015 |
| WO | 2015/108386 | A1 | 7/2015 |
| WO | 2016/010036 | A1 | 1/2016 |
| WO | 2016/078603 | A1 | 5/2016 |
| WO | 2017/101553 | A1 | 6/2017 |
| WO | 2018/049976 | A1 | 3/2018 |

OTHER PUBLICATIONS

English translation of KR 10-2014-0144809 A obtained from K-PION (Korean Patent information Online network) on Nov. 13, 2020, 24 pages. Publication date of KR 10-2014-0144809 A: Dec. 22, 2014. (Year: 2020).*

Derwent-ACC-No. 2015-00250P, English abstract of Patent-Family of KR 2014144809 publication date of Dec. 22, 2014, 3 pages (obtained from East database USPTO) (Year: 2014).*

English translation of JP 2009/0191142 A, 96 pages obtained Feb. 4, 2021 this translation of JP 2009-019142 a from J-PlatPat website. Publication date of JP 2009/0191142 A: Jan. 29, 2009. (Year: 2021).*

English translation of KR 10-2014-0144809.A from K-Pion (Korean Patent Information Online Network), 24 pages, obtained Feb. 3, 2021. The original KR 10-2014-0144809 was published Dec. 22, 2014. (Year: 2021).*

Accession No. CAN 462:123137 English abstractor KR 2014144809 a, inventors: Ku et al, obtained from SciFinder database on Feb. 3, 2021, 5 pages (Year: 2021).*

Office Action dated May 27, 2020, issued in counterpart KR Application No. 10-2018-7012617, with English Translation. (9 pages).

Notice of Allowance dated Oct. 9, 2019, issued in counterpart CN Application No. 201510937328.0, with English translation (3 pages).

Morand, Peter et al., "The Effect of Substituted Carboxylic Acids on Hepatic Cholesterogenesis", Journal of Medicinal Chemistry, US American Chemical Society, vol. 7, No. 7, Jul. 1, 1964, pp. 504-508; Cited in EESR dated Jul. 29, 2019.

Extended Search Report dated Jul. 29, 2019, issued in counterpart EP Application No. 16874611.9 (9 pages).

Office Action dated Nov. 21, 2019, issued in counterpart Korean application No. 10-2018-7019720, with English translation. (16 pages).

Office Action dated Feb. 3, 2020, issued in counterpart Chinese application No. 201610210118.6, with English translation. (14 pages).

Office Action dated Nov. 29, 2019, issued in counterpart Korean application No. 10-2018-7012617, with English translation. (19 pages).

Notice of Allowance dated Feb. 3, 2020, issued in counterpart Korean application No. 10-2018-7019720, with English translation. (3 pages).

Extended European Search Report dated Apr. 1, 2020, issued in EP application No. 17850178.9 (counterpart to U.S. Appl. No. 16/259,779)(14 pages).

International Search Report and Written Opinion dated Nov. 16, 2017, issued in International application No. PCT/CN2017/099294, with English Translation (counterpart to U.S. Appl. No. 16/259,779)(21 pages).

Office Action dated Aug. 22, 2019, issued in CN application No. 201710530354.0, with English translation (counterpart to U.S. Appl. No. 16/259,779)(21 pages).

Office Action dated Jan. 28, 2020, issued in JP application No. 2019-501481, with English Translation (counterpart to U.S. Appl. No. 16/259,779)(10 pages).

Office Action dated Mar. 27, 2020 issued in CN application No. 201610821992.3 (counterpart to U.S. Appl. No. 16/259,779)(8 pages).

Bachmann, et al., "The Rates of Dissociation of Pentaarylethanes", Contribution from the Chemistry Laboratory of the University of Michigan, Journal of Organic Chemistry, vol. 8(4), 1943, pp. 320-330.(11 pages).

Bolton, et al. The stability of Carbonium ions. Journal of the Chemical Society. (1964). pp. 1464-1466. (3 pages).

Chardonnens, et al., "Fluorenacenes and Fluorenaphenes, Synthesis of a Series of Indenofluorenes XVII. Methyl Derivatives of cis-Fluorenacene, trans-Fluorenacene and trans-Fluorenaphene", Helvetica Chimica Acta. vol. 57(3), 1974, pp. 585-599. (15 pages).

Horhold, et al., "Synthesis and Photoconductivity of Poly (2,7-fluorenylene-1,2-diphenylvinylen)", Studies on Poly (arylenevinylenes), Acta Polymerica, vol. 37(6), 1986, pp. 369-375. (7 pages).

Minabe, et al. Syntheses and Some Properties of 9,2':7',9"-, 9,2':9',9"and 9,4':9',9"-Terfluorene. Bulletin of the Chemical Society of Japan 1978 51:11, 3373-3376 (Year: 1978) (4 pages).

Park, et al., "Design and Synthesis of New Fluorene-Based Blue Light Emitting Polymer Containing Electron Donating Alkoxy Groups and Electron Withdrawing Oxadiazole", Macromolecular Research, vol. 15(3), 2007, pp. 216-220. (5 pages).

JubChem Bethesda (MD): National Library of Medicine (US), National Center for Biotechnology Information; 2004—. PubChem Compound Summary for CID 97070, Methanone, 9H-fluoren-2-ylphenyl-; [cited Oct. 8, 2020]. Available from: https:// pubchem.ncbi.nlm.nih.gov/compound/Methanone_-9H-fluoren-2-yl. (Year: 2004) (16 pages).

Xuong, et al., "Potential Chemical Pituitary Inhibitors of the Polyarylethylene Series", Department of Organic Chemistry, Radium Institute, University of Paris, Journal of the Chemical Society, 1952, pp. 3741-3744. (4 pages).

(56) References Cited

OTHER PUBLICATIONS

International Search Report dated May 10, 2018, issued in International Patent Application No. PCT/CN2018/076209, with English Translation (counterpart to U.S. Appl. No. 16/485,724). (5 pages).
Written Opinion of the International Searching Authority dated May 10, 2018, issued in International Patent Application No. PCT/CN2018/076209, with English Translation (counterpart to U.S. Appl. No. 16/485,724) (13 pages).
Office Action dated Aug. 6, 2020, issued in JP Application No. 2019-544745, with English translation (counterpart to U.S. Appl. No. 16/485,724) (14 pages).
Extended European Search Report dated Nov. 23, 2020, issued in EP Application No. 18755112.2 (counterpart to U.S. Appl. No. 16/485,724) (8 pages).
Database Registry[online]. STN International, Columbus, Ohio, USA, Oct. 27, 2016 (Oct. 27, 2016), CAS RN 2020359-04-8 (2 pages).
Robertson, David W. et al.: "Structure-Activity Relationships of (Arylalkyl)imidazole Anticonvulsants: Comparison of the (Fluorenylalkyl) imidazoles with Nafimidone and Denzimol", J. Med. Chem., 29, 9, 1577-1586 (1986). (10 pages).
International Search Report dated Dec. 30, 2016, issued in counterpart International Application No. PCT/CN2016/100601, with English translation. (5 pages).
Written Opinion dated Dec. 30, 2016, issued in counterpart International Application No. PCT/CN2016/100601, with English translation. (13 pages).
Office Action dated May 14, 2019, issued in counterpart JP Application No. 2018-530699, with English translation (8 pages).
Office Action dated Mar. 12, 2019, issued in counterpart JP Application No. 2018-517895, with English translation (9 pages).
Office Action dated Jul. 16, 2019, issued in counterpart JP Application No. 2018-517895, with English translation (16 pages).
Office Action dated Feb. 28, 2019, issued in counterpart CN Application No. 201510937328.0, with English translation (19 pages).
Office Action dated Jun. 4, 2019, issued in counterpart CN Application No. 201610210118.6, with English translation (15 pages).

* cited by examiner

FLUORENE POLYFUNCTIONAL PHOTOINITIATOR AND PREPARATION AND USE THEREOF, AND PHOTOSENSITIVE RESIN COMPOSITION CONTAINING FLUORENE PHOTOINITIATOR AND USE THEREOF

TECHNICAL FIELD

This invention belongs to the field of organic chemistry, and particularly to a fluorene polyfunctional photoinitiator and the preparation thereof, a photosensitive resin composition containing the fluorene photoinitiator and uses in the preparation of color filter films (RGBs), black matrices (BMs), photoresists, photo-spacers, ribs, wet films, dry films, and the like.

BACKGROUND ART

In display apparatuses such as liquid crystal displays and the like, a liquid crystal layer is typically provided between two substrates, and opposite electrodes are configured on each substrate, wherein a color filter layer formed of various pixels such as red (R), green (G), blue (B), black, and the like is configured on the inner side of one substrate and oppositely to the liquid crystal layer. Here, color weights of colors of R, G, and B are typically distinguished in forms of providing matrices.

At present, methods for producing color filters mainly include a staining method, a printing method, a pigment dispersion method, and an anode method, wherein the pigment dispersion method is the most widely used. The pigment dispersion method is a method comprising coating a photosensitive resin composition containing a coloring material on a transparent substrate and then performing image exposure and development as well as post-curing as occasion demands, and a color filter image is formed by repeating these processes. The color filter pixel obtained by this method has high positioning precision and high film thickness precision, excellent durability (such as light resistance, heat resistance, and the like), and few pin-hole defects.

In the production of color filters, BMs are typically configured between red, green, and blue patterns in a form of a grid shape, a bar shape, or a mosaic shape so as to prevent the failure of thin film transistors occurred due to light leakage or to improve the contrast by preventing color mixing between various colors. Therefore, it is required that the BM should have a relatively high light-shielding property. Therefore, how to form a high-efficiency BM at a low cost by using a photosensitive resin in which a light-shielding pigment or dye is dispersed has become a hot spot of studies. Generally, increasing the film thickness or increasing the content of the light-shielding pigment or dye is required to improve the light-shielding property of the BM. However, in the case that the light-shielding property is required in the whole light wavelength region, these measures will easily lead to significant failure of the photosensitive property of the composition, which exhibits the following aspects: cross-linking density differences occur among the exposed part, the unexposed part, and the bottom of exposure; the pigment which is insoluble in the developer reduces the developability so as to lead to reduced linearity of the pattern or peeling of the pattern, thereby generating residue; and so on.

At present, photosensitive compositions containing an oxime ester photoinitiator having carbazole or diphenyl sulfide as the main structure are commonly used. However, this type of photoinitiator has relatively high cost, which limits its use to some extent. Therefore, an affordable photoinitiator needs to be developed.

Conventional small molecular photoinitiators have excellent photosensitive property and solubility. However, there are problems, such as easy migration of photolysis fragments, large volatility, and the like, in practical applications. It is sought to address these deficiencies by increasing the molecular weight of the compound, but increased molecular weight will typically reduce the effect of photoinitiation.

The fluorene compound has a relatively large molecular weight, and its uses in ultraviolet photocuring of inks, paints, adhesives, and the like have been well known in the art. If the advantages of the fluorene compound and conventional small molecular photoinitiators can be combined to produce a polyfunctional photoinitiator, t not only he migration effects of photoinitiator molecules and photolysis products thereof are reduced and volatility issue is relieved, but also the photoinitiation efficiency may be improved by the combined action or even the synergistic effect between a plurality of different photoactive groups so as to further improve its application properties in the photosensitive composition. Therefore, there is a very high use value to seek a photoinitiator compound having this structure and property.

SUMMARY OF THE INVENTION

An object of this invention is first to provide a fluorene polyfunctional photoinitiator. This compound has simple synthesis, low cost, and good solubility, and has good application effects in photocurable compositions. Compared to conventional small molecular photoinitiators, it not only has excellent photoinitiation activity, but also has the advantages of low mobility, low odor property, good yellowing resistance, and the like.

The fluorene polyfunctional photoinitiator described in this invention has the structure as represented by the following formula (I):

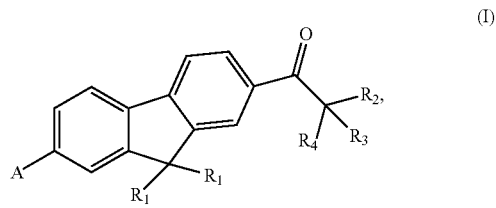

wherein, $R_1$ each independently represents hydrogen, halogen, a $C_1$-$C_{20}$ linear or branched alkyl group, a $C_4$-$C_{20}$ cycloalkylalkyl group, or a $C_2$-$C_{20}$ alkenyl group; $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, as $C_4$-$C_{20}$ alkylcycloalkyl group, or a $C_6$-$C_{20}$ aryl group, and $R_2$ and $R_3$ may be linked to each other to form a ring; $R_4$ represents a photoactive group; and A represents hydrogen, a nitro group, halogen, or a —CO—$CR_2R_3R_4$ group.

As a preferable technical solution, in the polyfunctional photoinitiator represented by formula (I) described above, $R_1$ each independently represents hydrogen, halogen, a $C_1$-$C_{10}$ linear or branched alkyl group, or a $C_4$-$C_{10}$ cycloalkylalkyl group. Further preferably, $R_1$ each independently represents hydrogen, a $C_1$-$C_4$ linear or branched alkyl group, or a $C_1$-$C_3$ alkyl group mono-substituted by a $C_3$-$C_6$ cycloalkyl group.

Preferably, $R_2$ and $R_3$ each independently represent a $C_1$-$C_{10}$ linear or branched alkyl group or a $C_4$-$C_{10}$ cycloalkylalkyl group, or $R_2$ and $R_3$ are linked to each other to form a $C_3$-$C_{10}$ cycloalkyl group. Further preferably, $R_2$ and $R_3$ each independently represent a $C_1$-$C_4$ linear or branched alkyl group or a $C_4$-$C_8$ cycloalkylalkyl group, or $R_2$ and $R_3$ are linked to each other to form a $C_3$-$C_6$ cycloalkyl group.

Preferably, $R_4$ represents a hydroxy group or a N-morpholinyl group.

Preferably, A represents hydrogen, a nitro group, or a —CO—$CR_2R_3R_4$ group. When a —CO—$CR_2R_3R_4$ group is taken, $R_2$, $R_3$, and $R_4$ have the same definitions as described above.

This invention further comprises a preparation method of the fluorene polyfunctional photoinitiator represented by formula (I) described above, comprising the steps of:

(1) Friedel-Crafts reaction, wherein
a raw material a and a raw material b are subjected to Friedel-Crafts reaction in an organic solvent under the catalysis of aluminum trichloride or zinc chloride to obtain an intermediate a,

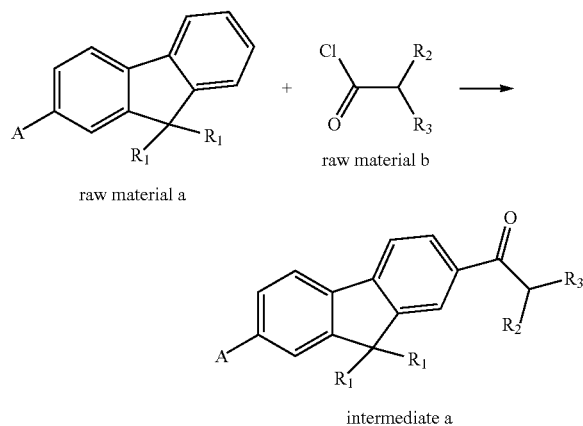

(2) bromination reaction, wherein
the intermediate a and liquid bromine are subjected to bromination reaction in the presence of a solvent to generate an intermediate b,

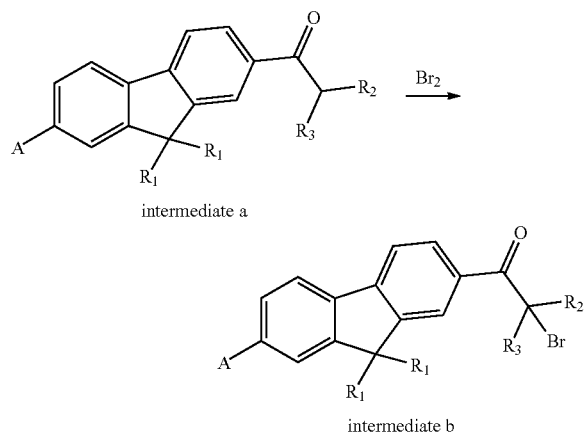

(3) dehalogenation reaction, wherein
the intermediate b is subjected to hydrolysis or reaction with a compound containing a non-hydroxy photoactive group to obtain a product of interest,

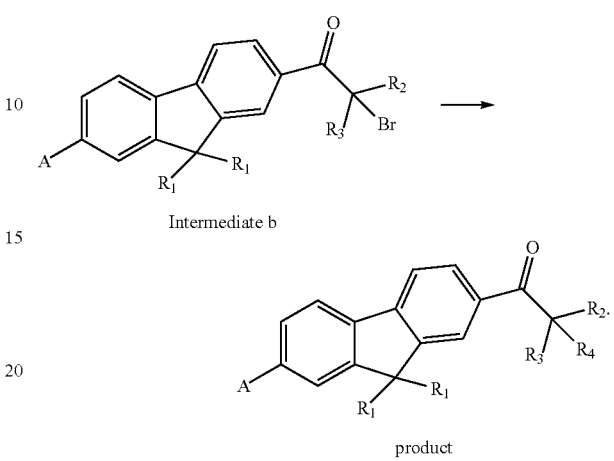

It will be easily understood by a person skilled in the art that when the raw material a is a fluorene which is merely substituted by $R_1$ (i.e., A is taken as H), the proportions of raw materials in the reaction are adjusted to allow A to remain hydrogen or become a —CO—$CR_2R_3R_4$ group via Friedel-Crafts, bromination, and dehalogenation reactions so as to obtain two products having different structures.

All of the raw materials used in the preparation method described above are compounds which are known in the prior art, commercially available, or conveniently prepared by known synthetic methods. Furthermore, reactions involved in steps (1) to (3) are all conventional reactions for synthesizing similar compounds in the art. On the basis of knowing the idea of synthesis disclosed in this invention, specific reaction conditions will be easily determined with respect to a person skilled in the art.

In step (1), which is Friedel-Crafts reaction, the reaction temperature is typically −10 to 30° C. The type of the organic solvent used in the reaction is not specially limited, as long as raw materials can be dissolved and there is no adverse influence on the reaction, and dichloromethane, dichloroethane, benzene, xylene, and the like are preferable.

In step (2), the temperature of the bromination reaction is typically 30 to 50° C. The type of the solvent used is not specially limited, as long as raw materials can be dissolved and there is no adverse influence on the reaction, and dichloromethane, dichloroethane, benzene, xylene, and the like are preferable.

In step (3), which is dehalogenation reaction, the intermediate b is subjected to hydrolysis or reaction with a compound containing a non-hydroxy photoactive group to introduce a photoactive group into the structure so as to generate a photoinitiator of interest.

When the intermediate b is dehalogenated by hydrolysis, a hydroxy group may be introduced at the position of $R_4$. The reaction system further comprises a solvent system composed of an organic solvent and water as well as an inorganic base and a phase transfer catalyst in addition to the intermediate b. The organic solvent may be selected from dichloromethane, dichloroethane, benzene, xylene, acetonitrile, and the like; the inorganic base is preferably an inorganic strong base such as KOH, NaOH, and the like; the phase transfer catalyst is preferably a quaternary ammonium salt phase transfer catalyst, such as tetrabutyl ammonium bromide, tetrapropyl ammonium bromide, tetra-n-butyl ammonium, triethylbenzyl ammonium chloride, tetrabutyl ammonium hydrogen sulfate, and the like. The reaction temperature of hydrolysis is typically 60 to 150° C.

When the intermediate b is dehalogenated by reaction with a compound containing a non-hydroxy photoactive group, a corresponding photoactive group may be introduced at the position of $R_4$, and the temperature of the reaction is typically 40 to 160° C. The solvent may be or may be not used in the reaction system as needed. The type of the solvent used is not specially limited, as long as raw materials can be dissolved and there is no adverse influence on the reaction, and dichloromethane, dichloroethane, benzene, xylene, acetonitrile, and the like are preferable. As an example of the compound containing a non-hydroxy photoactive group, it may be, for example, morpholine, thiomorpholine, and the like.

Accordingly, this invention also relates to use of the photoinitiator represented by formula (I) described above in the field of photocuring. Particularly, it may be used for the production of paints coated on base materials such as plastics, metal, glasses, ceramics, woods, walls, optical fibers, and the like; protective film materials such as hard coating agents, antifouling films, antireflective films, impact buffering films, and the like; photocurable adhesives, stickers, photo-decomposable paints, coating films, and moldable matters; optical recording media such as holographic image materials and the like; optical moldable resins, for example, inks (resins) for 3D printing, photoresists for the production of electronic circuits and semiconductors, photoresists for electronic materials such as color filters, black matrices, dry films, wet films, and the like in displays), and so on; interlayer insulating films, light extraction films, brightening films, and sealing materials; inks for printing such as screen printing, offset printing, gravure printing, and the like, and photocurable inks for inkjet printing; optical members such as lenses, lens arrays, optical waveguides, light guide plates, light diffusion plates, diffraction elements, and the like; photo-spacers, ribs, materials for nanoimprint, and the like.

Preferably, the use includes uses in the production of color filter films, photoresists, black matrices, photo-spacers, ribs, wet films, dry films, inks, coatings, and adhesives.

By introducing a small molecular active group to a fluorene compound, as compared to conventional small molecular photoinitiators, the polyfunctional photoinitiator of this invention not only has excellent photoinitiation activity, but also has the advantages of low mobility, low odor property, good yellowing resistance, and the like, as well as excellent film-forming property.

In view of the circumstance described above, a further object of this invention is to provide a novel photosensitive resin composition. It has the advantage of relatively low cost and has good exposure sensitivity (i.e., high photosensitivity) and developability. In the case that the system contains a high content of a light-shielding agent or a exposure dose is very low, it has a complete pattern, clear development, high resolution, and excellent adhesion with substrates after curing.

In order to achieve the object described above, the following technical solutions are adopted.

A photosensitive resin composition comprises the following components: (A) a radical polymerizable compound; (B) a photoinitiator, which is selected from at least one of compounds with the fluorene compound represented by formula (I) as the main structure or derivative compounds thereof:

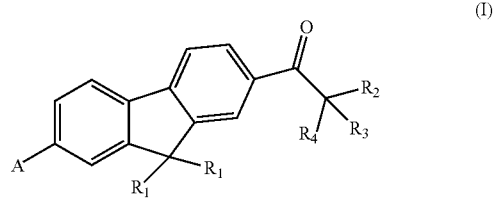

(I)

wherein, A represents hydrogen, halogen, a nitro group, a $C_1$-$C_{10}$ linear or branched alkyl group, a $C_3$-$C_{10}$ alkylcycloalkyl, a $C_4$-$C_{10}$ alkylcycloalkyl or cycloalkylalkyl group, wherein —$CH_2$— in A may be substituted by O, N, S, or C(=O); X represents a connection symbol or a carbonyl group; $R_1$ represents hydrogen, halogen, a $C_1$-$C_{20}$ linear or branched alkyl group, a $C_4$-$C_{20}$ cycloalkylalkyl group, or a $C_2$-$C_{20}$ alkenyl group, wherein —$CH_2$— in $R_1$ may be substituted by O, N, S, or C(=O), and a ring may be formed between $R_1$s; $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group, wherein —$CH_2$— in $R_2$ and $R_3$ may be substituted by O, N, S, or C(=O), and $R_2$ and $R_3$ are linked to each other to form a ring; $R_4$ represents a photoactive group of a hydroxy group, a N-morpholinyl group, or a N-dialkyl group; and (C) optionally, a colorant; and (D) optionally, an alkali-soluble resin, wherein preferably the parts by mass of the alkali-soluble resin are greater than 0 and less than or equal to 80 parts, and more preferably 20 to 60 parts.

The polymerizable composition of this invention may be mixed and used with an alkali-soluble resin, as long as the alkali-soluble resin (D) acts as an adhesive. When an image pattern is formed, the developer used in the procedure of developing treatment is preferably a soluble alkali developer, preferably an alkali-soluble resin as a carboxy-containing copolymer, particularly preferably a copolymer of an olefinically unsaturated monomer having one or more carboxy groups and another copolymerizable olefinically unsaturated monomer.

Furthermore, the above-described compound with the fluorene compound represented by formula (I) as the main structure preferably comprises the following structure:

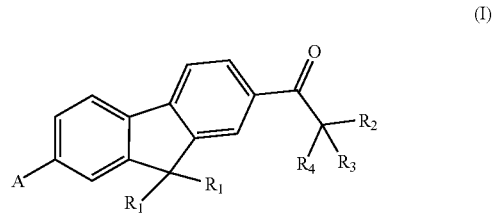

(I)

wherein A represents hydrogen, a nitro group, or a $C_1$-$C_{10}$ linear or branched alkyl group; $R_1$ represents hydrogen, a $C_1$-$C_{20}$ linear or branched alkyl group, or a $C_1$-$C_{20}$ linear or branched alkyl group substituted by O, N, S, or C(=O); $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, or a $C_6$-$C_{20}$ aryl group, wherein —$CH_2$— in $R_4$ and $R_5$ may be substituted by O, N, S, or C(=O), and $R_4$ and $R_5$ are linked to each other to form a ring; and $R_4$ represents a hydroxy group, a N-morpholinyl group, or a N-dialkyl group.

Furthermore, the compound with the fluorene compound represented by formula (I) as the main structure preferably comprises the structure as shown below:

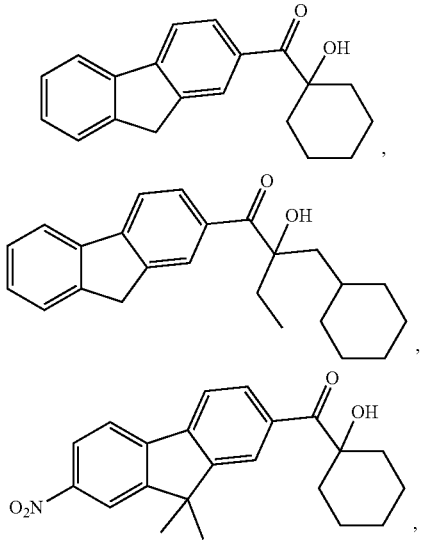

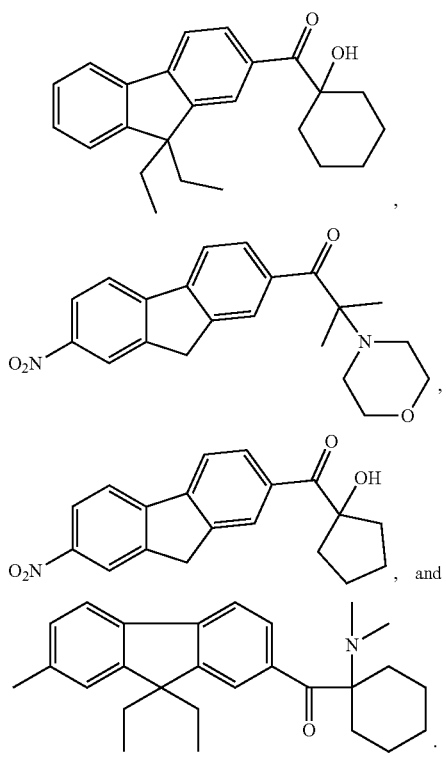

Furthermore, the derivative compound with the fluorene compound represented by formula (I) as the main structure is preferably a compound represented by formula (VI) or (VIII):

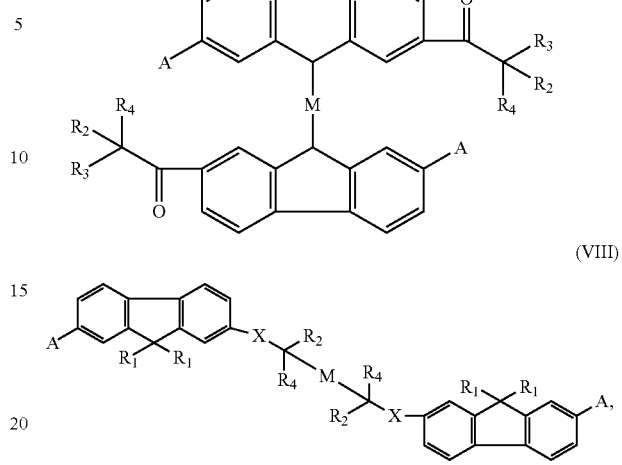

wherein M represents a linking group formed by dimerization of $R_1$, $R_2$, or $R_3$, M is blank, a $C_1$-$C_{24}$ linear or branched alkylene group, or a $C_6$-$C_{36}$ arylene or heteroarylene group, and in M, —$CH_2$— is optionally substituted by sulfur, oxygen, NH, or a carbonyl group, and the hydrogen atom is optionally substituted by OH or $NO_2$.

Furthermore, the derivative compound with the fluorene compound represented by formula (I) as the main structure is preferably a compound having the following structure:

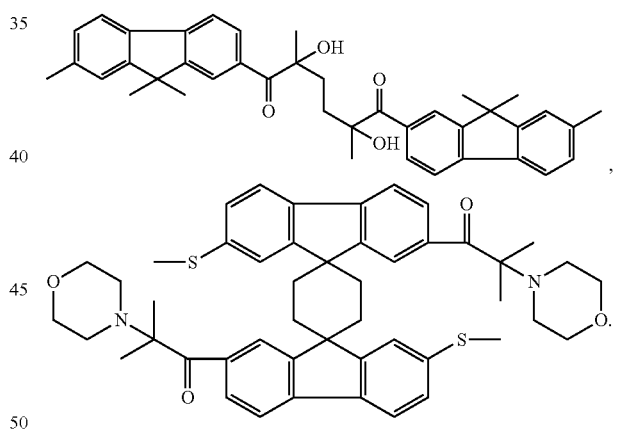

Another object of this invention is to provide use of the photosensitive resin composition described above in the field of photocuring. The use includes uses in the production of color filter films, photoresists, black matrices, photospacers, ribs, wet films, dry films, inks, coatings, and adhesives.

Another object of this invention is to provide use of the photosensitive resin composition described above in preparing photoresists for color filter films, black matrices, photospacers, ribs, and dry films.

The proportioning of various components in the photosensitive resin composition described in this invention is reasonable. The photocurable composition has very high light sensitivity, can be cross-linked and cured at a very low exposure dose, and has a very good curing effect. A film made from the composition has a smooth edge, no defects and scum, a good and clear pattern, and high hardness. The color filter produced has high optical transparency and no light leakage. The production thereof is finished at a very low exposure dose, and it has good precision, flatness, and durability.

DESCRIPTION OF EMBODIMENTS

It is to be indicated that Examples in this application and features in the Examples may be combined with each other without being conflicted. This invention will be illustrated in detail in conjunction with Examples below.

As analyzed in the Background Art, in the prior art, the oxime ester photoinitiator and the matrix resin have insufficient solubilities. In order to solve this problem, a typical embodiment of this application provides a fluorene polyfunctional photoinitiator, having the structure as represented by the following formula (I):

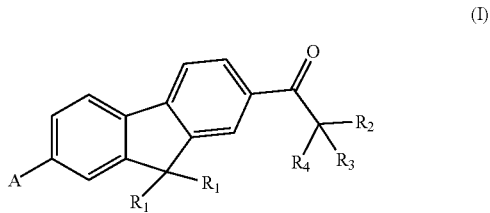

(I)

wherein $R_1$ each independently represents hydrogen, halogen, a $C_1$-$C_{20}$ linear or branched alkyl group, a $C_4$-$C_{20}$ cycloalkylalkyl group, or a $C_2$-$C_{20}$ alkenyl group; $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, as $C_4$-$C_{20}$ alkylcycloalkyl group, or a $C_6$-$C_{20}$ aryl group, and $R_2$ and $R_3$ may be linked to each other to form a ring; $R_4$ represents a photoactive group; and A represents hydrogen, a nitro group, halogen, or a —CO—$CR_2R_3R_4$ group.

The compound described above has simple synthesis, low cost, and good solubility, and has excellent storage stability and film-forming property when used in photocurable compositions.

In another typical embodiment of this application, there is provided a photosensitive resin composition. The photosensitive resin composition of this invention comprises components (A) and (B), and optionally components (C) and (D). Since having the structure described above is the effective binding of the fluorene functional group, the carbonyl group, and the photoactive group in the compound of (I), it has excellent dissolution property, storage stability, and initiation property.

The above-described photosensitive resin composition of this invention has high photosensitivity, good developability, high resolution, and excellent adhesion with substrates. It is highly suitable to produce black matrices having high light-shielding property, color filters having high fineness and high quality, and liquid crystal display apparatuses. It also can be used in aspects of photo-spacers, ribs, and the like.

Furthermore, the proportioning of various components in the photosensitive resin composition is reasonable. The photocurable composition has very high light sensitivity, can be cross-linked and cured at a very low exposure dose, and has a very good curing effect. A film made from the composition has a smooth edge, no defects and scum, a good and clear pattern, and high hardness. The color filter produced has high optical transparency and no light leakage. The production thereof is finished at a very low exposure dose, and it has good precision, flatness, and durability.

Respective components will be illustrated in more detail below.

<Component (A) a Radical Polymerizable Compound>

In the photosensitive resin composition of this invention, the component (A) is a compound having a radical polymerizable olefinically unsaturated bond or/and an epoxy compound. The so-called compound having a radical polymerizable olefinically unsaturated bond is just a compound having at least one or more radical polymerizable olefinically unsaturated bonds in the molecule, and the compound described above may have a chemical morphology of monomer, oligomer, polymer, and the like.

Examples of this compound having a radical polymerizable olefinically unsaturated bond may include unsaturated carboxylic acids and salts, esters, carbamates, amides, and acid anhydrides thereof such as acrylic acid esters, methacrylic acid esters, itaconic acid, crotonic acid, isocrotonic acid, maleic acid, and the like, acrylonitrile, styrene, and vinyl ether, as well as radical polymerizable compounds such as various unsaturated polyesters, unsaturated polyethers, unsaturated polyamides, unsaturated urethanes, and the like. This invention is not limited thereto.

Further, as the acrylic acid compound described in this invention, the following compounds may be exemplified: methyl acrylate, ethyl acrylate, propyl acrylate, isopropyl acrylate, butyl acrylate, isopentyl acrylate, hexyl acrylate, 2-ethylhexyl acrylate, octyl acrylate, decyl acrylate, dodecyl acrylate, octadecyl acrylate, isobornyl acrylate, cyclohexyl acrylate, dicyclopentenyl acrylate, dicyclopentenyloxyethyl acrylate, benzyl acrylate, 2-hydroxyethyl acrylate, 2-hydroxypropyl acrylate, 2-hydroxy-3-chloropropyl acrylate, 2-hydroxy-3-phenoxypropyl acrylate, 2-hydroxy-3-allyloxypropyl acrylate, 2-acryloyloxyethyl-2-hydroxypropyl phthalate, 2,2,2-trifluoroethyl acrylate, 1,3-butanediol methyl ether acrylate, butoxyethyl acrylate, β-carboxyethyl acrylate, monoacryloyloxyethyl succinate, ω-carboxy polycaprolactone monoacrylate, trimethylsilyloxyethyl acrylate, biphenyl-2-acryloyloxyethyl phosphate, triethylene glycol diacrylate, tetraethylene glycol diacrylate, bisphenol A diacrylate, EO-modified bisphenol A diacrylate, PO-modified bisphenol A diacrylate, hydrogenated bisphenol A diacrylate, EO-modified hydrogenated bisphenol A diacrylate, PO-modified hydrogenated bisphenol A diacrylate, bisphenol F diacrylate, EO-modified bisphenol F diacrylate, PO-modified bisphenol F diacrylate, EO-modified tetrabromobisphenol A diacrylate, tricyclodecane dimethylol diacrylate, glycerol PO-modified triacrylate, trimethylolpropane triacrylate, pentaerythritol tetraacrylate, dipentaerythritol tetraacrylate, dipentaerythritol pentaacrylate monopropionate, dipentaerythritol hexaacrylate, tetramethylolmethane tetraacrylate, and the like.

Further, as the methacrylic acid compound described in this invention, the following compounds may be exemplified: methyl methacrylate, ethyl methacrylate, hydroxyethyl methacrylate, propyl methacrylate, isopropyl methacrylate, butyl methacrylate, isopentyl methacrylate, hexyl methacrylate, 2-hexyl methacrylate, 2-ethylhexyl methacrylate, octyl methacrylate, decyl methacrylate, dodecyl methacrylate, octadecyl methacrylate, isobornyl methacrylate, cyclohexyl methacrylate, dicyclopentenyl methacrylate, dicyclopentenyloxyethyl methacrylate, benzyl methacrylate, 2-hydroxyethyl methacrylate, 2-hydroxypropyl methacrylate, 2-hydroxy-3-chloropropyl methacrylate, 2-hydroxy-3- phenoxypropyl methacrylate, 2,2,2-trifluoroethyl methacrylate, 2,2,3,3-tetrafluoropropyl methacrylate, 1H-hexafluoroisopropyl methacrylate, 2-methoxy ethyl methacrylate, 1,3-butanediol methyl ether methacrylate, butoxyethyl methacrylate, methoxytriethylene glycol methacrylate, methoxypolyethylene glycol #400 methacrylate, methoxy dipropylene glycol methacrylate, methoxy tripropylene glycol methacrylate, methoxy polypropylene glycol methacrylate, ethoxy diethylene glycol methacrylate, 2-ethylhexyl carbitol methacrylate, tetrahydrofurfuryl methacrylate, phenoxyethyl methacrylate, pentaerythritol tetramethacrylate, dipentaerythritol pentamethacrylate monopropionate, dipentaerythritol hexamethacrylate, and the like.

Further, as the radical polymerizable compound described in this invention, the following may also be exemplified: allylglycidyl ether, diallyl phthalate, triallyl trimellitate, triallyl isocyanurate, acrylamide, N-hydroxymethyl acrylamide, diacetone acrylamide, N,N-dimethyl acrylamide, N,N-diethyl acrylamide, N-isopropyl acrylamide, acryloylmorpholine, styrene, p-hydroxystyrene, p-chlorostyrene, p-bromostyrene, p-methylstyrene, vinyl acetate, monochlorovinyl acetate, vinyl benzoate, vinyl pivalate, vinyl butyrate, vinyl laurate, divinyl adipate, and the like.

With respect to the radical polymerizable compound (A) of this invention, only one kind may be used, and two or more kinds may also be used by being mixed at an arbitrary ratio in order to improve desirable properties.

The amount of the component (A) used in the photosensitive resin composition may be 0.1-100 parts by mass, preferably 30-80 parts by mass, and more preferably 40-70 parts by mass.

<Component (B) Photoinitiator>

The component (B) photoinitiator used in this invention is selected from at least one of a fluorene compound represented by formula (I) or formula (II) and a derivative compound with the compound represented by formula (I) or formula (II) as the main structure. This photoinitiator may be only composed of a fluorene compound represented by formula (I) or formula (II) or a derivative compound with it as the main structure, or may be a combination of two compounds.

Further, compounds represented by formulas (I) and (II) described in this invention are respectively:

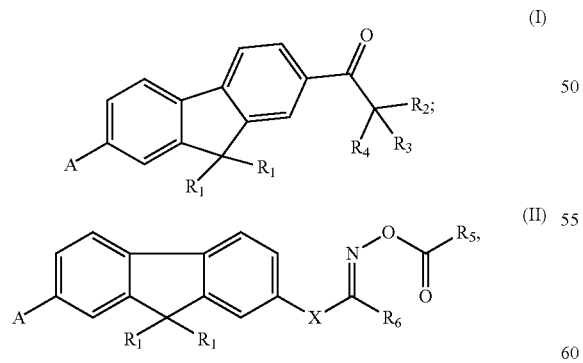

wherein A represents hydrogen, halogen, a nitro group, a $C_1$-$C_{10}$ linear or branched alkyl group, a $C_3$-$C_{10}$ alkylcycloalkyl, a $C_4$-$C_{10}$ alkylcycloalkyl or cycloalkylalkyl group, wherein —$CH_2$— in A may be substituted by O, N, S, or C(=O); X represents a connection symbol or a carbonyl group; $R_1$ represents hydrogen, halogen, a $C_1$-$C_{20}$ linear or branched alkyl group, a $C_4$-$C_{20}$ cycloalkylalkyl group, or a $C_2$-$C_{20}$ alkenyl group, wherein —$CH_2$— in $R_1$ may be substituted by O, N, S, or C(=O), and a ring may be formed between $R_1$s; $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group, wherein —$CH_2$— in $R_2$ and $R_3$ may be substituted by O, N, S, or C(=O), and $R_2$ and $R_3$ are linked to each other to form a ring; $R_4$ represents a photoactive group of a hydroxy group, a N-morpholinyl group, or a N-dialkyl group; and $R_5$ and $R_6$ each independently represent a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group, wherein —$CH_2$— in $R_2$ and $R_3$ may be substituted by O, N, S, or C(=O).

As preferable embodiments, fluorene compounds represented by formula (I) or formula (II) include compounds represented by the following structures:

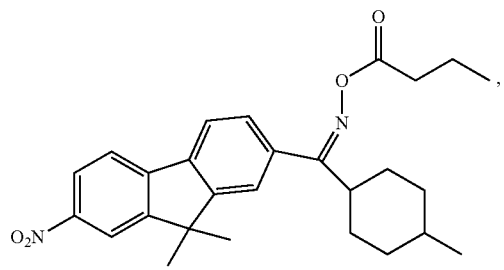

compound 1

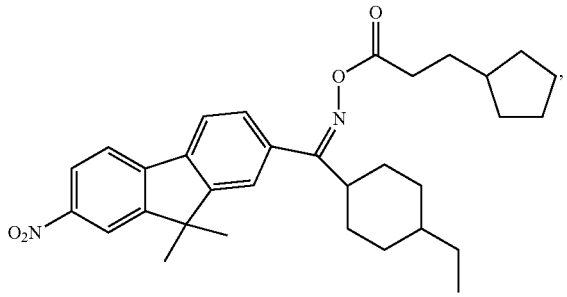

compound 2

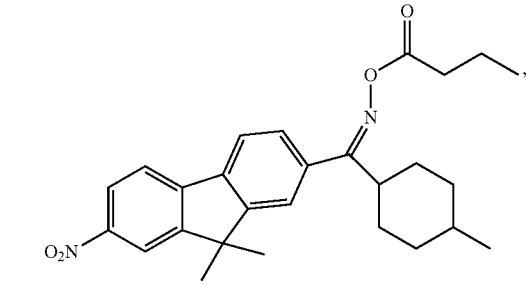

compound 3

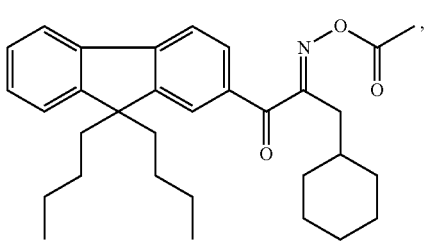

compound 4 compound 5
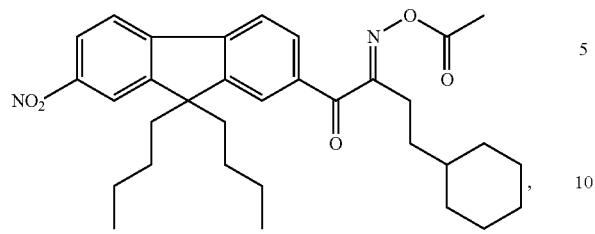
compound 6
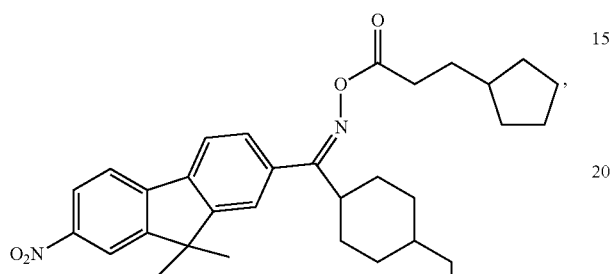
compound 7
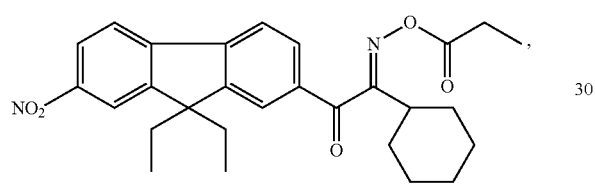
compound 8
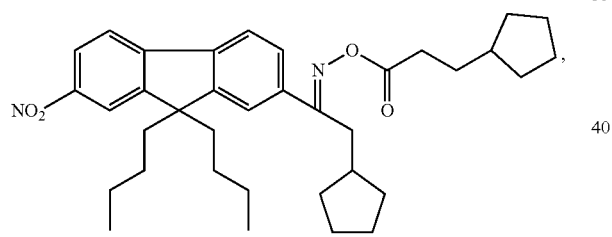
compound 9
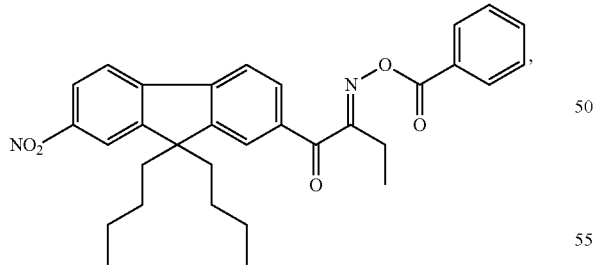
compound 10
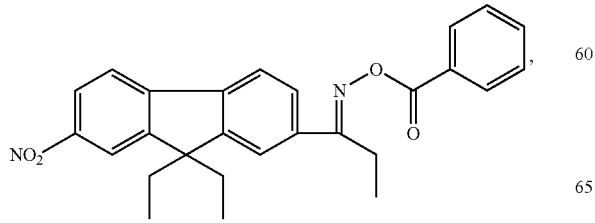
compound 11
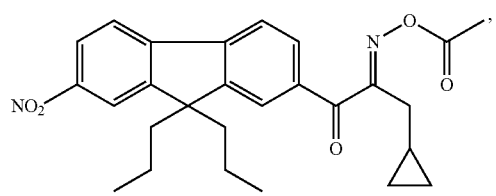
compound 12
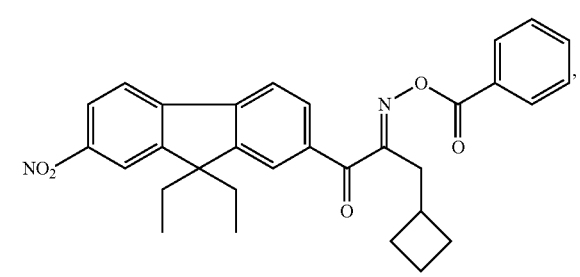
ompound 13
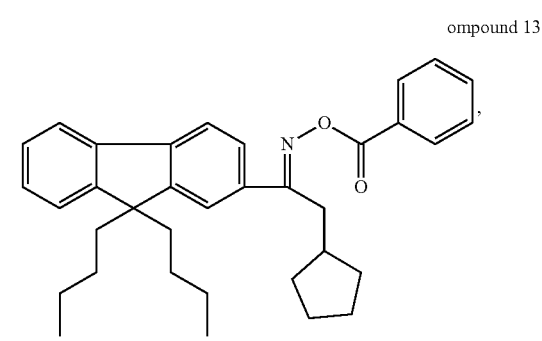
compound 14
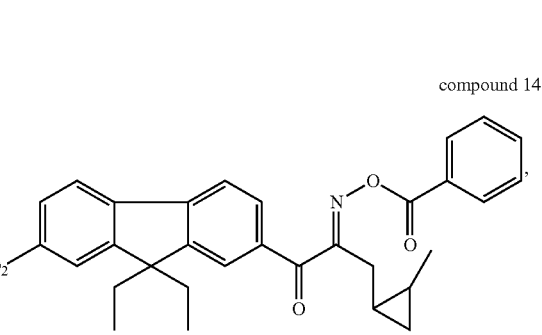
compound 15
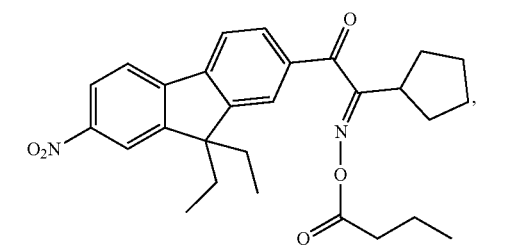

15
-continued
compound 16
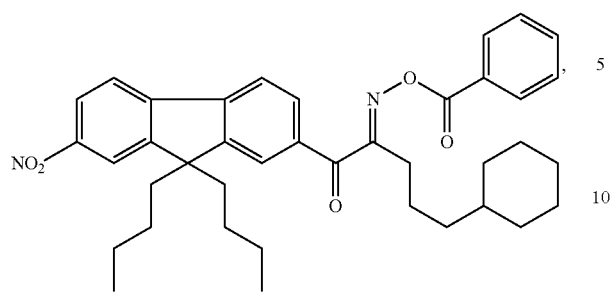
compound 17
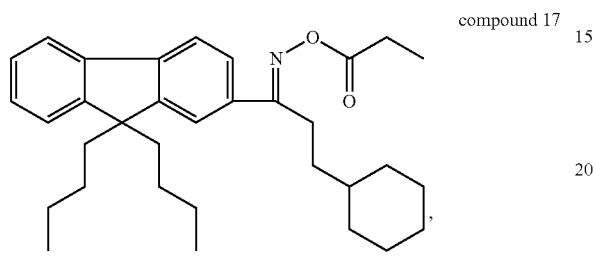
compound 18
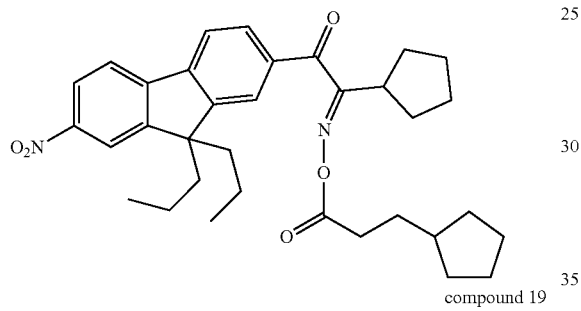
compound 19
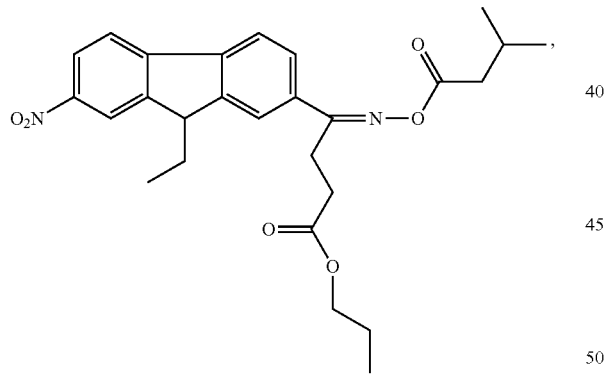
compound 20
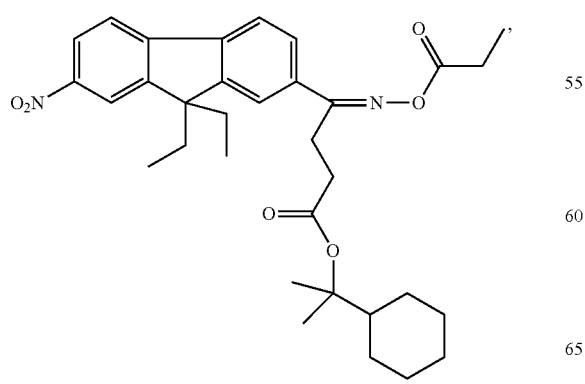
16
-continued
compound 21
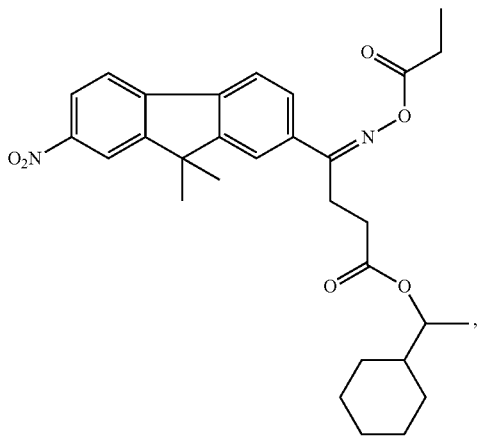
compound 22
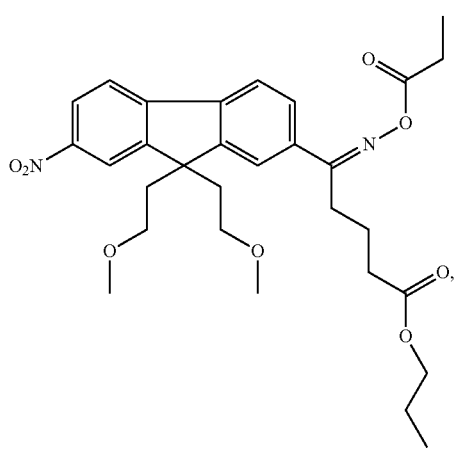
compound 23
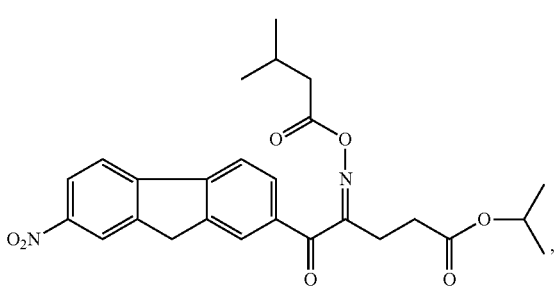
compound 24
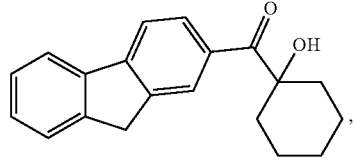
compound 25
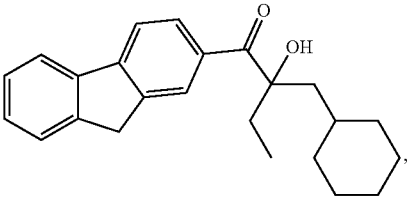

compound 26

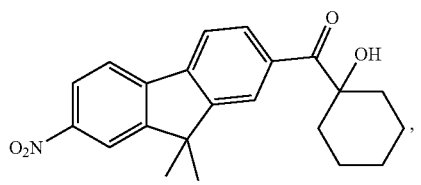

compound 27

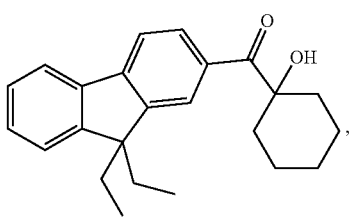

compound 28

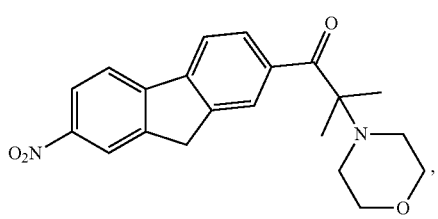

compound 29

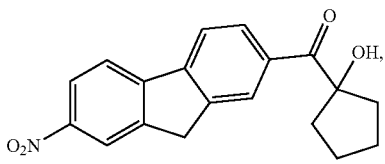

compound 30

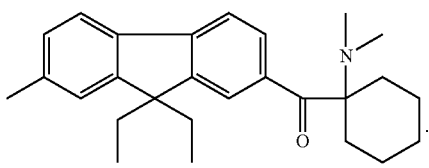

The above-described derivative compound with the compound represented by formula (I) or formula (II) as the main structure refers to a derivative obtained by substitution or mutual linking of branched chains in the case of maintaining the main structure of the compound of formula (I) or formula (II) unchanged. When used as a photoinitiator in this invention, the derivative compound with the compound represented by formula (I) or formula (II) as the main structure is the compound represented by the following formula (III), (IV), (V), (VI), or (VIII):

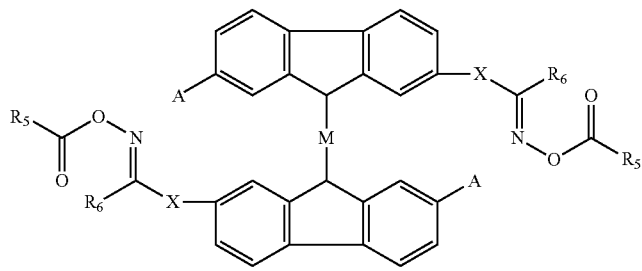

(III)

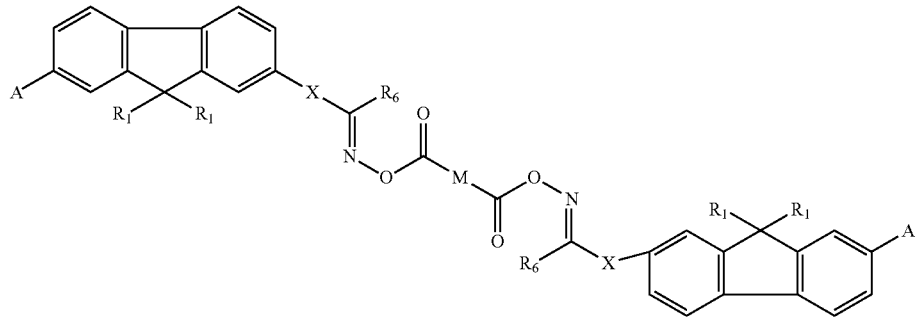

(IV)

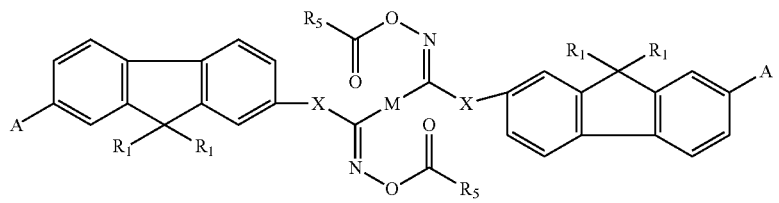

(V)

(VII)

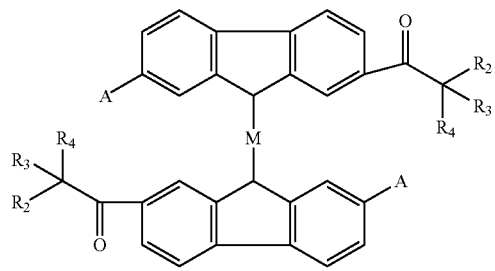

(VIII)

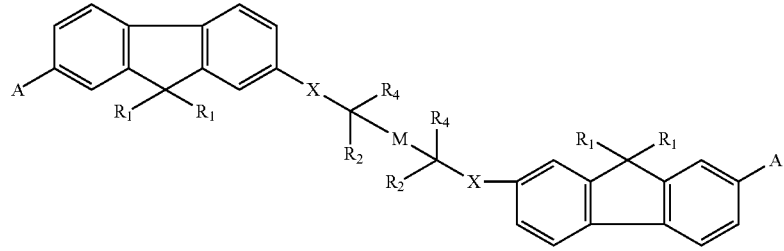

wherein M represents a linking group formed by dimerization of $R_1$, $R_2$, $R_3$, $R_5$, or $R_6$, M is blank, a $C_1$-$C_{24}$ linear or branched alkylene group, or a $C_6$-$C_{36}$ arylene or heteroarylene group, and in M, —$CH_2$— is optionally substituted by sulfur, oxygen, NH, or a carbonyl group, and the hydrogen atom is optionally substituted by OH or $NO_2$.

Exemplarily, the derivative compound described above may be a compound having the following structure:

compound 31

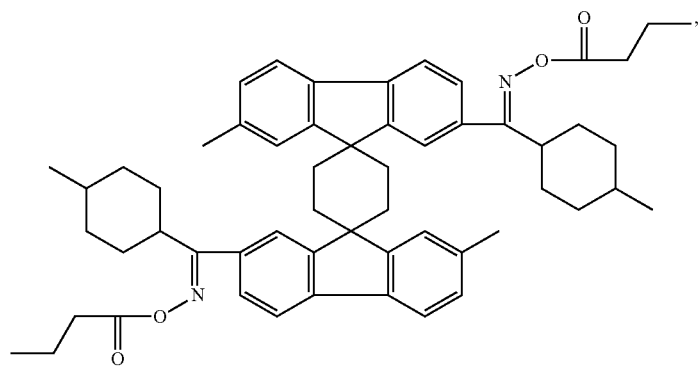

compound 32

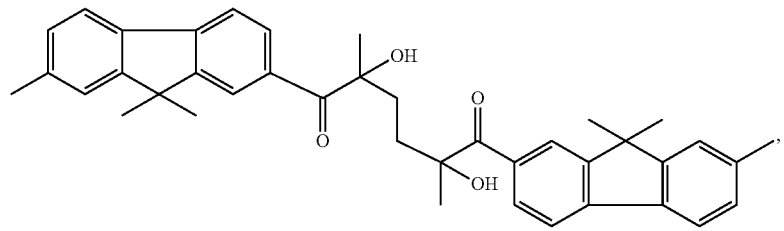

-continued compound 33

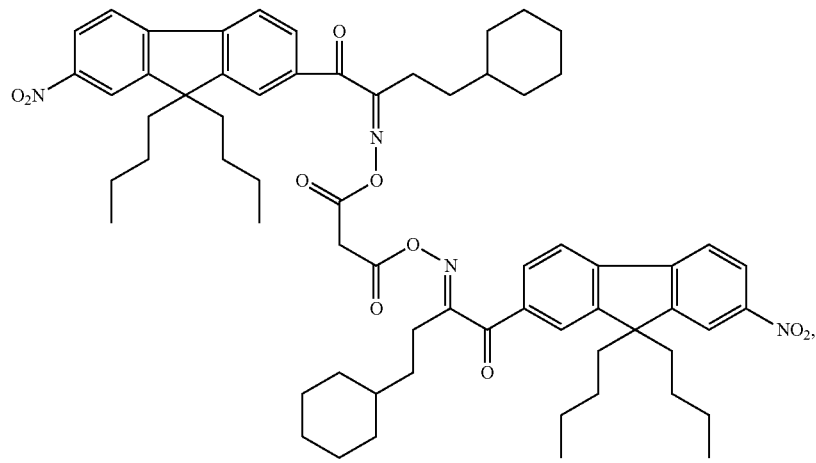

compound 34

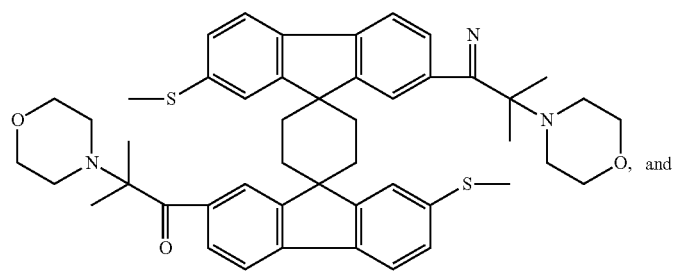
and compound 35

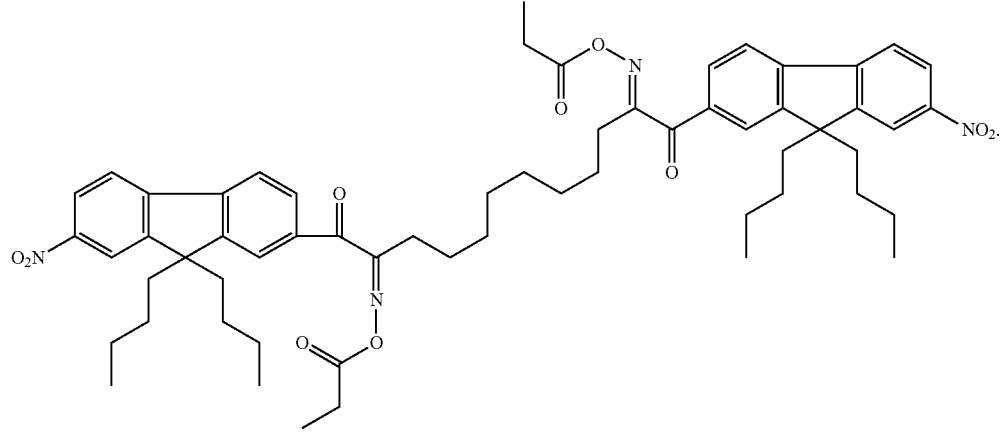

The amount of the component (B) used in the photosensitive resin composition is preferably 1 to 5 parts by mass.

<Component (C) Colorant>

The photosensitive resin composition of this invention may further contain the component (C) colorant. Without limitation, by containing a colorant, the composition of this invention may be used to form a color filter of a liquid crystal display; and when a light-shielding agent is used as a colorant, the composition may be used to form a black-matrix cathode ray tube in a color filter of a display apparatus.

The type of the component (C) colorant is not particularly limited in this invention. It may be those compounds which are classified as pigments in color index (C.I.; published by The Society of Dyers and Colourists), preferably colorants having the following C.I. numbers, for example:

C.I. Pigment Yellow 1 (since C.I. Pigment Yellow is identical below, only the number is recorded), 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, 185; C.I. Pigment Orange 1 (since C.I. Pigment Orange is identical below, only the number is recorded), 5, 13, 14, 16, 17, 24, 34, 36, 38, 40, 43, 46, 49, 51, 55, 59, 61, 63, 64, 71, 73; C.I. Pigment Violet 1 (since C.I. Pigment Violet is identical below, only the number is recorded), 19, 23, 29, 30, 32, 36, 37, 38, 39, 40, 50; C.I. Pigment Red 1 (since C.I. Pigment Red is identical below, only the number is recorded), 2, 3, 4, 5, 6, 7, 8, 9, 10, 11, 12, 14, 15, 16, 17, 18, 19, 21 and 22, 23, 30, 31, 32, 37, 38, 40, 41 and 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, 265; C.I. Pigment Blue 1 (since C.I. Pigment Blue is identical below, only the number is recorded), 2, 15, 15:3, 15:4, 15:6, 16, 22, 60, 64, 66; C.I. Pigment Green 7, C.I. Pigment Green 36, C.I. Pigment Green 37; C.I. Pigment Brown 23, C.I. Pigment Brown 25, C.I. Pigment Brown 26, C.I. Pigment Brown 28; and C.I. Pigment Black 1, C.I. Pigment Black 7.

When a light-shielding agent is selected as the colorant, a black pigment is preferably used as the light-shielding agent. As the black pigment, the following may be exemplified: carbon black, titanium black, and metal oxides, complex oxides, metal sulfides, metal sulfates, or metal carbonates of copper, iron, manganese, cobalt, chromium, nickel, zinc, calcium, silver, etc. Among these black pigments, carbon black having high light-shielding property is preferably used, which may be a common carbon black such as channel carbon black, furnace carbon black, thermal carbon black, lamp carbon black, and the like, and channel carbon black having excellent light-shielding property is preferably used; and a resin coated-carbon black may also be used. Additionally, in order to adjust the color tone of carbon black, the organic pigment listed above may be suitably added as an auxiliary pigment. It is practically demonstrated that it may exhibit very good developability and pattern integrity even if a black pigment having high light-shielding property is used in the photosensitive resin composition of this invention.

The amount of the component (C) used in the photosensitive resin composition is 0-50 parts by mass, preferably 5-40 parts by mass.

<Component (D) Alkali-Soluble Resin>

The polymerizable composition of this invention may be mixed and used with an alkali-soluble resin, as long as the alkali-soluble resin (D) acts as an adhesive. When an image pattern is formed, the developer used in the procedure of developing treatment is preferably a soluble alkali developer, preferably an alkali-soluble resin as a carboxy-containing copolymer, particularly preferably a copolymer (hereinafter simply referred to as "carboxy-containing copolymer" (R)) of an olefinically unsaturated monomer having one or more carboxy groups (hereinafter simply referred to as "carboxy-containing unsaturated monomer" (P)) and another copolymerizable olefinically unsaturated monomer (hereinafter simply referred to as "copolymerizable unsaturated monomer" (Q)).

As the carboxy-containing unsaturated monomer, the following compounds may be exemplified: unsaturated monocarboxylic acids such as acrylic acid, methacrylic acid, crotonic acid, α-chloroacrylic acid, cinnamic acid, and the like; unsaturated dicarboxylic acids or acid anhydrides thereof such as maleic acid, maleic anhydride, fumaric acid, itaconic acid, itaconic anhydride, citraconic acid, citraconic anhydride, mesaconic acid, and the like; tribasic or higher unsaturated polycarboxylic acids or acid anhydrides thereof; mono[(meth)acryloyloxyalkyl] esters of dibasic or higher polycarboxylic acids such as mono(2-acryloyloxyethyl) succinate, mono(2-methylacryloyloxyethyl) succinate mono(2-acryloyloxyethyl) phthalate, mono(2-methylacryloyloxyethyl) phthalate, and the like; mono(meth)acrylic acid esters of polymers having a carboxy group and a hydroxy group on both ends such as ω-carboxy polycaprolactone monoacrylate, ω-carboxy polycaprolactone monomethacrylate, and the like; and so on.

Furthermore, as the copolymerizable unsaturated monomer, the following may be exemplified, for example: aromatic vinyl compounds such as styrene, α-methylstyrene, o-vinyltoluene, m-vinyltoluene, p-vinyltoluene, p-chlorostyrene, o-methoxystyrene, m-methoxystyrene, p-methoxystyrene, o-vinylbenzyl methyl ether, m-vinylbenzyl methyl ether, p-vinylbenzyl methyl ether, o-vinylbenzyl glycidyl ether, m-vinylbenzyl glycidyl ether, p-vinylbenzyl glycidyl ether, and the like; indenes such as indene, 1-methylindene, and the like; glycidyl esters of unsaturated carboxylic acids such as glycidyl acrylate, glycidyl methacrylate, and the like; vinyl esters of carboxylic acids such as vinyl acetate, vinyl propionate, vinyl butyrate, vinyl benzoate, and the like; unsaturated ethers such as vinylmethylether, vinylethylether, allylglycidyl ether, and the like; vinyl cyanide compounds such as acrylonitrile, methacrylonitrile, α-chloroacrylonitrile, vinylidene cyanide, and the like; unsaturated amides such as acrylamide, methacrylamide, α-chloroacrylamide, N-2-hydroxyethylacrylamide, N-2-hydroxyethylmethacrylamide, and the like; unsaturated imides such as maleimide, N-phenylmaleimide, N-cyclohexylmaleimide, and the like; aliphatic conjugated dienes such as 1,3-butadiene, isoprene, chlorobutadiene, and the like; polymers having macromers such as a monoacryl group or a monomethacryloyl group at the end of molecular chains, such as polystyrene, polymethyl acrylate, polymethyl methacrylate, poly-n-butyl acrylate, poly-n-butyl methacrylate, polysiloxane, and the like; and so on. These copolymerizable unsaturated monomers may be used alone or in combination of two or more.

A preferable carboxy-containing copolymer in this invention (hereinafter referred to as "carboxy-containing copolymer (R)") is obtained by polymerizing (P) with (Q). The (P) uses acrylic acid and/or methacrylic acid as an essential component, and as desired, further contains a carboxy-containing unsaturated monomer component, which is selected from at least one compound of mono(2-acryloyloxyethyl) succinate, mono(2-methyl acryloyloxyethyl) succinate, ω-carboxy polycaprolactone monoacrylate, and ω-carboxy polycaprolactone monomethacrylate. The (Q) is selected from at least one of styrene, methyl acrylate, methyl methacrylate, 2-hydroxyethyl acrylate, 2-hydroxyethyl methacrylate, allyl acrylate, allyl methacrylate, benzyl acrylate, benzyl methacrylate, glycerol monoacrylate, glycerol monomethacrylate, N-phenylmaleimide, a polystyrene macromer, and a polymethyl methacrylate macromer.

As specific examples of the carboxy-containing copolymer (R), the following may be exemplified: a (meth)acrylic acid/methyl (meth)acrylate copolymer, a (meth)acrylic acid/benzyl (meth)acrylate copolymer, a (meth)acrylic acid/2-hydroxyethyl (meth)acrylate/benzyl (meth)acrylate copolymer, a (meth)acrylic acid/methyl (meth)acrylate/polystyrene macromer copolymer, a (meth)acrylic acid/methyl (meth)acrylate/polymethyl methacrylate macromer copolymer, a (meth)acrylic acid/benzyl (meth)acrylate/polystyrene macromer copolymer, a (meth)acrylic acid/benzyl (meth)acrylate/polymethyl methacrylate macromer copolymer, a (meth)acrylic acid/2-hydroxyethyl (meth)acrylate/benzyl (meth)acrylate/polystyrene macromer copolymer, a (meth)acrylic acid/2-hydroxyethyl (meth)acrylate/benzyl (meth)acrylate/polymethyl methacrylate macromer copolymer, a methacrylic acid/styrene/benzyl (meth)acrylate/N-phenylmaleimide copolymer, a (meth)acrylic acid/mono[2-(meth)acryloyloxyethyl] succinate/styrene/benzyl (meth)acrylate/

N-phenylmaleimide copolymer, a (meth)acrylic acid/mono [2-(meth)acryloyloxyethyl] succinate/styrene/allyl (meth) acrylate/N-phenylmaleimide copolymer, a (meth)acrylic acid/styrene/benzyl (meth)acrylate/glycerol mono(meth) acrylate/N-phenylmaleimide copolymer, a (meth)acrylic acid/ω-carboxy polycaprolactone mono(meth)acrylate/styrene/benzyl (meth)acrylate/glycerol mono(meth)acrylate/N-phenylmaleimide copolymer, and the like. The substituent present in the carboxy-containing copolymer molecule may be further modified by other materials.

In this invention, the alkali-soluble resin (D) may be used alone or in combination of two or more.

The amount of the component (D) used in the photosensitive resin composition is 0-80 parts by mass, preferably 20-60 parts by mass.

<Other Optional Components>

According to application requirements of the product, one or more macromolecular or polymeric compounds may be further added to this composition as needed to improve the application properties of the composition in use. These macromolecular or polymeric compounds may be polyols or polyester polyols. Also, polymers without reactive functional groups may be selectively added. These polymer are usually resins containing an acidic functional group such as a phenolic hydroxy group, a hydroxy group, and the like, and may also be used together with other photoinitiators.

Additionally, other aids commonly used in the art may be also selectively added to the photosensitive resin composition of this invention, and include, but are not limited to, sensitizers, dispersants, surfactants, solvents, and the like.

The polymer of interest may be obtained by polymerizing the polymerizable composition of this invention in polymerization reaction by giving the energy generated by ultraviolet, visible light, near infrared, electron beams, and the like. As a light source for giving the energy, light sources having the dominant wavelength which emits light in a wavelength region of 250 nm to 450 nm are preferable. As the light source having the dominant wavelength which emits light in a wavelength region of 250 nm to 450 nm, various light sources may be exemplified, such as ultrahigh-pressure mercury lamps, high-pressure mercury lamps, medium-pressure mercury lamps, mercury-xenon lamps, metal halide lamps, large-power metal halide lamps, xenon lamps, pulse light-emitting xenon lamps, deuterium lamps, Led lamps, fluorescent lamps, Nd-YAG third homonic wave laser, He—Cd laser, nitrogen laser, Xe-Cl excimer laser, Xe-F excimer laser, semiconductor-excited solid laser, and the like.

<Preparation and Use>

Various components were weighed based on the amounts thereof and uniformly mixed, and the photosensitive resin composition of this invention may be thus obtained. This is a well-known conventional technology with respect to a person skilled in the art. The photosensitive composition described in this invention can be used not only in the field of normal photocuring such as ink, paints, adhesives, and the like, but also in the field of high-level photocuring such as the preparation of color filter films, photoresists, black matrices, photo-spacers, ribs, wet films, and dry films.

A further object of this invention is to provide use of the photosensitive resin composition described above in preparing photoresists for color filter films, black matrices, photo-spacers, ribs, and dry films.

Techniques for producing RGBs, BMs, photo-spacers, and the like using photosensitive resin compositions by the processes of photocuring and lithography have been well known to the skilled person in the art, and typically comprise the steps of:

i) dissolving a photosensitive resin composition in a suitable organic solvent and uniformly mixing to obtain a liquid-like composition; ii) uniformly coating the liquid-like composition on a substrate using a coater, for example a spin coater, a wire bar coater, a roll coater, a spray coater, etc.; iii) performing prebaking for drying to remove the solvent; iv) attaching a mask plate onto a sample to perform exposure, and subsequently developing to remove unexposed regions; and v) performing postbaking to obtain a dry photoresist film having a desirable shape.

The photoresist film containing a black pigment is exactly the black matrix, BM, and the photoresist films containing red, green, and blue pigments are exactly R, G, and B photoresists, respectively.

PREPARATION EXAMPLES

Example 1

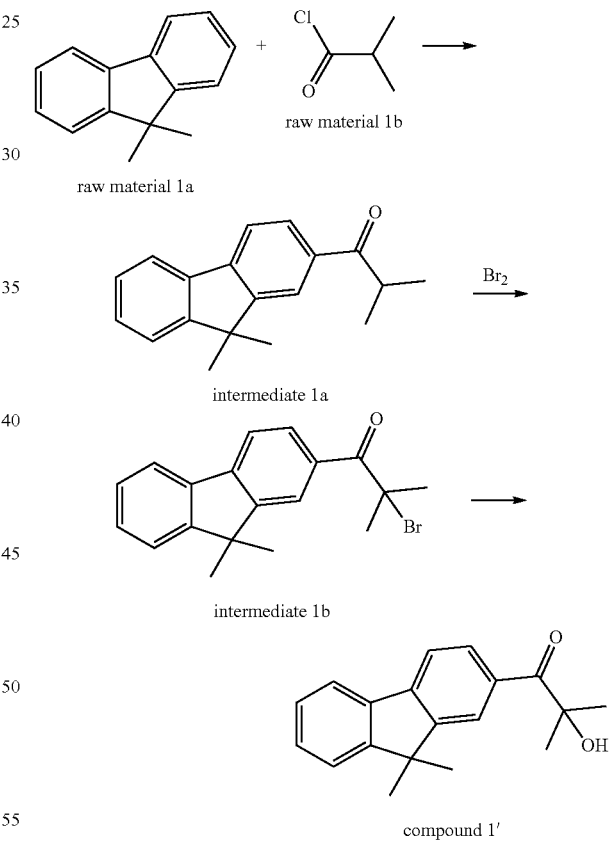

Step (1): Preparation of Intermediate 1a 97 g of a raw material 1a, 67 g of aluminum trichloride, and 100 mL of dichloromethane were added to a 500 mL four-necked flask, and the temperature was reduced to 0° C. by an ice water bath. A mixed solution of 54 g of a raw material 1b, i.e., isobutanoyl chloride and 50 mL of dichloromethane was dropped and the temperature was controlled to 10° C. or below, and the dropping was finished in approximately 2 h. Stirring was continued for 2 h after completion of dropping, and liquid phase tracking was performed until the reaction was complete. The materials were then slowly poured with stirring into dilute hydrochloric acid formulated with 800 g of ice water and 100 mL of concentrated hydrochloric acid (37%), and were then poured into a separation funnel to separate a lower layer, which was a dichloromethane layer. 50 mL of dichloromethane was used to continue to wash the water layer. Dichloromethane layers were combined, the dichloromethane layer was washed with a 5% aqueous sodium bicarbonate solution (300 mL for each time, 3 times), and the dichloromethane layer was washed with water until pH was neutral. The dichloromethane layer was dried with 150 g of anhydrous magnesium sulfate, and after filtration, dichloromethane solution of the product was evaporated by rotation. Recrystallization with methanol was performed and drying in an oven at 60° C. was performed for 2 h to obtain 121 of an intermediate 1a with a yield of 92% and a purity of 98%.

The structure characterization data of this intermediate product were as shown below.

$^1$H-NMR (CDCl$_3$, 500 MHz): 1.2146-1.3005 (6H, d), 1.6788 (6H, s), 3.3005-3.3994 (1H, m), 7.2881-8.0231 (7H, m).

MS (m/z): 265 (M+1)$^+$.

Step (2): Preparation of Intermediate 1b 49 g of the intermediate 1a and 50 mL of dichloromethane were added to a 500 mL four-necked flask, the temperature was increased to 40° C. with stirring, and a tail gas absorbing apparatus was attached. 80 mL of a dichloromethane solution containing 16 g of bromine was dropped, and the dropping was finished in approximately 2 h. Stirring was continued for 2 h with maintaining temperature, and materials were poured into a 25% ice water solution of NaOH and stirred for 30 min. A dichloromethane layer was separated with a separation funnel, and 50 mL of dichloromethane was used again to extract the water layer. The dichloromethane layers were combined and washed with water to become neutral. After evaporation by rotation, recrystallization with methanol was performed to obtain 60 g of a white solid, i.e., the intermediate 1b, with a yield of 86% and a purity of 98%.

The structure characterization data of this intermediate product were as shown below.

$^1$H-NMR (CDCl$_3$, 500 MHz): 1.6642 (6H, s), 2.0629 (6H, s), 7.3080-7.8346 (7H, m);

MS (m/z): 344 (M+1)$^+$.

Step (3): Synthesis of Compound 1'

34 g of the intermediate 1b, 50 mL of dichloroethane, 0.2 g of tetrabutylammonium bromide and 75 g of aqueous NaOH solution with a concentration of 40% were added to a 250 mL four-necked flask, which were refluxed with heating at 80° C. for 2 h, liquid phase tracking was performed until the reaction was complete. The temperature was then reduced to room temperature, a dichloroethane layer was separated with a separation funnel, the dichloroethane layer was washed with water to become neutral, and dichloroethane was removed via evaporation by rotation. Recrystallization with methanol was performed to obtain 24 g of a white solid product, i.e., the compound 1', with a yield of 87% and a purity of 99%.

The structure of the product was determined by hydrogen nuclear magnetic resonance spectroscopy and mass spectrometry. $^1$H-NMR (CDCl$_3$, 500 MHz): 1.5062 (6H, s), 1.6669 (6H, s), 2.0755-2.2992 (1H, s), 7.2251-7.8325 (7H, m). MS (m/z): 281 M+1)$^+$.

Example 2

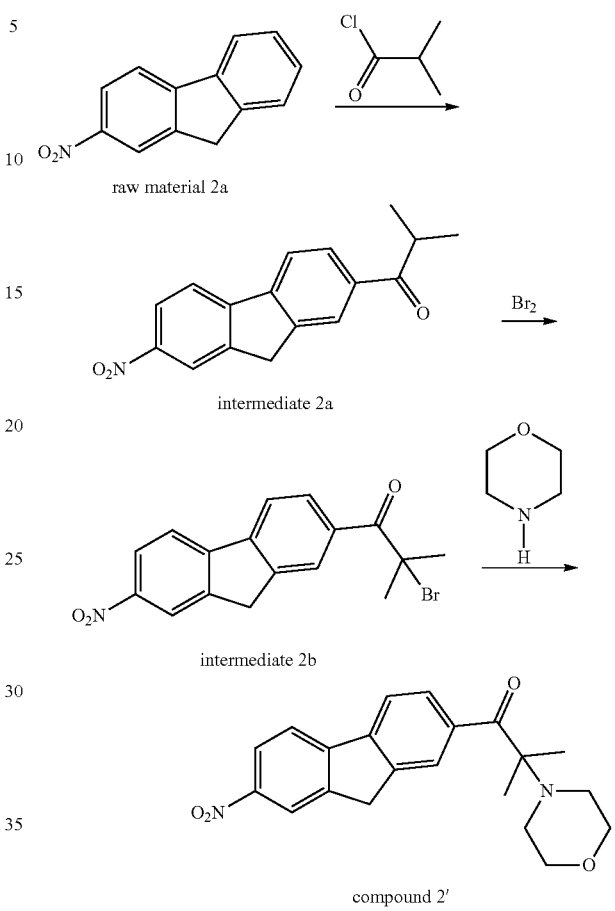

Step (1): Preparation of Intermediate 2a 106 g of a raw material 2a, 67 g of aluminum trichloride, and 100 mL of dichloromethane were added to a 500 mL four-necked flask, and the temperature was reduced to 0° C. by an ice water bath. A mixed solution of 54 g of isobutanoyl chloride and 50 mL of dichloromethane were dropped and the temperature was controlled to 10° C. or below, and the dropping was finished in approximately 2 h. Stirring was continued for 2 h after completion of dropping, and liquid phase tracking was performed until the reaction was complete. The materials were then slowly poured with stirring into dilute hydrochloric acid formulated with 800 g of ice water and 100 mL of concentrated hydrochloric acid, and were then poured into a separation funnel to separate a lower layer, which was a dichloromethane layer. 50 mL of dichloromethane was used to continue to wash the water layer. Dichloromethane layers were combined, the dichloromethane layer was washed with a 5% aqueous sodium bicarbonate solution (300 mL for each time, 3 times), and the dichloromethane layer was washed with water until pH was neutral. The dichloromethane layer was dried with 150 g of anhydrous magnesium sulfate, and after filtration, dichloromethane solution of the product was evaporated by rotation. Recrystallization with methanol was performed and drying in an oven at 60° C. was performed for 2 h to obtain 128 g of an intermediate 2a with a yield of 91% and a purity of 98%.

The structure characterization data of this intermediate product were as shown below. ¹H-NMR(CDCl₃, 500 MHz): 1.2007-1.2316(6H, d), 3.3208-3.3447(1H, m), 3.8676-3.8801(2H, s),7.9111-8.0352(6H, m)MS(m/z):282(M+1)⁺.

Step (2): Preparation of Intermediate 2b 56 g of the intermediate 2a and 50 mL of dichloromethane were added to a 500 mL four-necked flask, the temperature was increased to 40° C. with stirring, and a tail gas absorbing apparatus was attached. 80 mL of a dichloromethane solution containing 16 g of bromine was dropped, and the dropping was finished in approximately 2 h. Stirring was continued for 2 h with maintaining temperature, and materials were poured into a 25% ice water solution of NaOH and stirred for 30 min. A dichloromethane layer was separated with a separation funnel, and 50 mL of dichloromethane was used again to extract the water layer. The dichloromethane layers were combined and washed with water to become neutral. After evaporation by rotation, recrystallization with methanol was performed to obtain 61 g of a white solid, i.e., the intermediate 2b, with a yield of 86% and a purity of 98%.

The structure characterization data of this intermediate product were as shown below.

¹H-NMR (CDCl₃, 500 MHz): 2.0632 (6H, s), 3.8679 (2H, s), 7.9083-8.0956 (6H, m).

MS (m/z): 361 (M+1)⁺.

Step (3): Synthesis of Compound 2'

36 g of the intermediate 2b and 60 g of morpholine were added to a 250 mL four-necked flask, which were refluxed with heating at 130° C. for 60 h, liquid phase tracking was performed until the reaction was complete. The reaction liquid was then poured into water and stirred. A creamy white solid was precipitated, and was subjected to suction filtration and washed with water. Recrystallization with methanol was performed to obtain 22.3 g of a white solid, i.e., the compound 2', with a yield of 60% and a purity of 99%.

The structure of the product was determined by hydrogen nuclear magnetic resonance spectroscopy and mass spectrometry. ¹H-NMR (CDCl₃, 500 MHz): 1.3613(6H, s), 2.3629-2.4101(4H, t), 3.6765-3.7242(4H, t), 3.8740 (2H, s), 7.9225-8.4366(6H, m). MS(m/z): 367(M+1)⁺.

Example 3

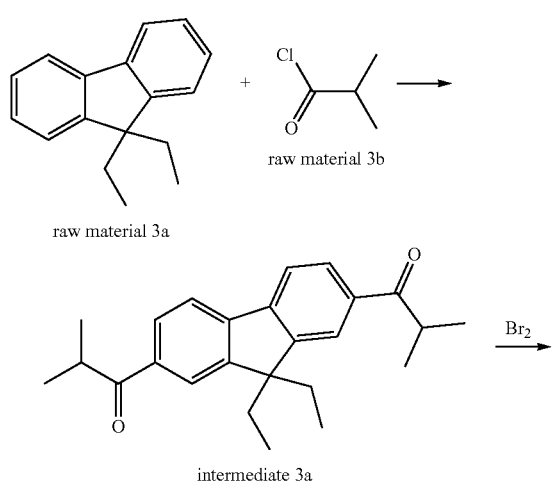

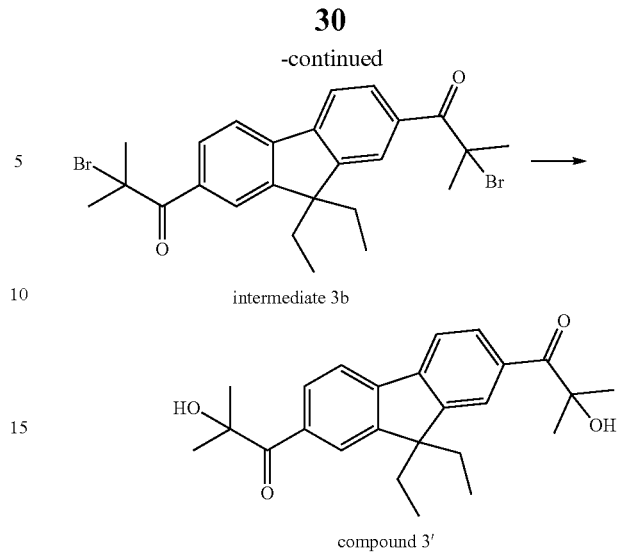

Step (1): Preparation of Intermediate 3a 111 g of a raw material 3a, 134 g of aluminum trichloride, and 200 mL of dichloromethane were added to a 1000 mL four-necked flask, and the temperature was reduced to 0° C. by an ice water bath. A mixed solution of 107 g of isobutanoyl chloride and 100 mL of dichloromethane were dropped and the temperature was controlled to 10° C. or below, and the dropping was finished in approximately 2 h. Stirring was continued for 2 h after completion of dropping, and liquid phase tracking was performed until the reaction was complete. The materials were then slowly poured with stirring into dilute hydrochloric acid formulated with 800 g of ice water and 150 mL of concentrated hydrochloric acid, and were then poured into a separation funnel to separate a lower layer, which was a dichloromethane layer. 100 mL of dichloromethane was used to continue to wash the water layer. Dichloromethane layers were combined, the dichloromethane layer was washed with a 5% aqueous sodium bicarbonate solution (300 mL for each time, 3 times), and the dichloromethane layer was washed with water until pH was neutral. The dichloromethane layer was dried with 200 g of anhydrous magnesium sulfate, and after filtration, dichloromethane solution of the product was evaporated by rotation. Recrystallization with methanol was performed and drying in an oven at 60° C. was performed for 2 h to obtain 163 g of an intermediate 3a with a yield of 90% and a purity of 98%.

The structure characterization data of this intermediate product were as shown below.

¹H-NMR(CDCl₃, 500 MHz): 0.9667-1.0002(6H, t), 1.2149-1.2355(12H, d), 1.9062-1.9147(2H, m), 3.3265-3.4272(2H, m),7.9327-8.1753(6H, m).

MS (m/z):363(M+1)⁺.

Step (2): Preparation of Intermediate 3b 73 g of the intermediate 3a and 80 mL of dichloromethane were added to a 500 mL four-necked flask, the temperature was increased to 40° C. with stirring, and a tail gas absorbing apparatus was attached. 100 mL of a dichloromethane solution containing 32 g of bromine was dropped, and the dropping was finished in approximately 2 h. Stirring was continued for 2 h with maintaining temperature, and materials were poured into a 25% ice water solution of NaOH and stirred for 30 min. A dichloromethane layer was separated with a separation funnel, and 80 mL of dichloromethane was used again to extract the water layer. The dichloromethane layers were combined and washed with water to become neutral. After evaporation by rotation, recrystallization with methanol was performed to obtain 87 g of a white solid, i.e., the intermediate 3b, with a yield of 84% and a purity of 98%.

The structure characterization data of this intermediate product were as shown below.

¹H-NMR(CDCl₃, 500 MHz): 0.9664(6H, t), 1.8991-1.9132(4H, m), 2.0632(12H, s), 3.8679 (2H, s),7.9111-8.1506(6H, m).

MS(m/z):521(M+1)⁺.

Step (3): Synthesis of Compound 3'

52 g of the intermediate 3b, 100 mL of dichloroethane, 0.3 g of tetrabutylammonium bromide and 150 g of aqueous NaOH solution with a concentration of 40% were added to a 500 mL four-necked flask, which were refluxed with heating at 80° C. for 2 h, liquid phase tracking was performed until the reaction was complete. The temperature was then reduced to room temperature, a dichloroethane layer was separated with a separation funnel, the dichloroethane layer was washed with water to become neutral, and dichloroethane was evaporated by rotation and removed. Recrystallization with methanol was performed to obtain 33 g of a white solid product, i.e., the compound 3', with a yield of 85% and a purity of 99%.

The structure of the product was determined by hydrogen nuclear magnetic resonance spectroscopy and mass spectrometry. ¹H-NMR(CDCl₃, 500 MHz): 0.9599-0.9754(6H, t), 1.4927(12H, s), 1.8976-1.9088 (4H, t), 2. 0146-2.1961 (2H, s), 7.91571-8.1677(6H, m). MS(m/z):395(M+1)⁺.

Examples 4-14

Referring to the methods illustrated in Examples 1-3, compounds 4'-14' shown in Table 1 below were prepared from corresponding raw materials.

TABLE 1

| | Structure | MS (m/z) | ¹H-NMR (CDCl₃, 500 MHz) |
|---|---|---|---|
| Compound 4' | 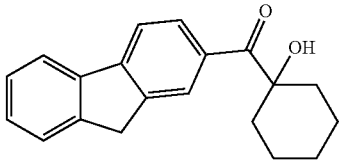 [SMILES: O=C(c1ccc2c(c1)Cc1ccccc1-2)C1(O)CCCCC1] | 293 | 1.4376-1.4453 (6H, m), 1.7402-1.7753 (4H,t), 2.002-2.123 (1H, t), 3.8671 (2H,s), 7.2861-7.9968 (7H, m) |
| Compound 5' | 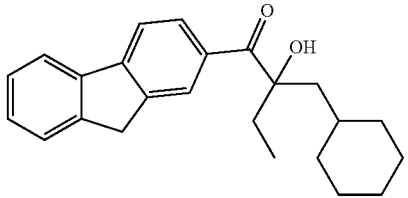 [SMILES: CCC(O)(CC1CCCCC1)C(=O)c1ccc2c(c1)Cc1ccccc1-2] | 349 | 0.9665-0.9806 (3H, t), 1.4007-1.4473 (11H, m), 1.5342-1.5756 (2H,d), 1.6294-1.6346 (2H,m), 1.9998-2.1052 (1H,s), 3.8688 (2H,s), 7.2863-8.0001 (7H, m) |
| Compound 6' | 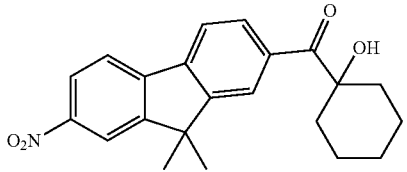 [SMILES: CC1(C)c2cc(C(=O)C3(O)CCCCC3)ccc2-c2ccc([N+](=O)[O-])cc21] | 366 | 1.4401-1.4577 (6H,m), 1.6772-1.7442(10H,m), 1.9978-2.0216 (1H,s), 7.9023-8.0001 (6H,m) |
| Compound 7' | 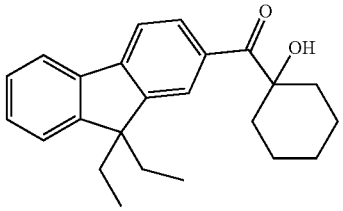 [SMILES: CCC1(CC)c2ccccc2-c2ccc(C(=O)C3(O)CCCCC3)cc21] | 349 | 0.9665-1.0032 (6H, t), 1.4377-1.4497 (6H, m), 1.7432-1.8927 (8H, m), 1.9997-2.1378(1H,s), 7.2865-8.0028(7H,m) |
| Compound 8' | 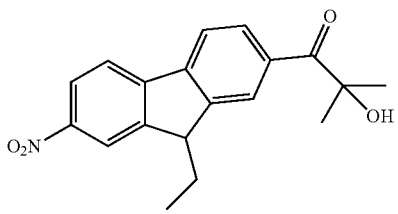 [SMILES: CCC1c2cc(C(=O)C(C)(C)O)ccc2-c2ccc([N+](=O)[O-])cc21] | 326 | 0.9667-0.9987(3H,t), 1.4776 (6H,s), 1.9522-2.2165(3H,m), 3.8554-3.8667(1H,t), 7.9253-8.4335(6H,m) |

TABLE 1-continued

| Structure | MS (m/z) | ¹H-NMR (CDCl₃, 500 MHz) |
|---|---|---|
| Compound 9' | 367 | 1.3633 (6H,s), 2.3669-2.3802(4H,t), 3.6578-3.8776 (6H, m), 7.9004-8.4882 (6H, m) |
| Compound 10' | 349 | 1.4002-1.4886 (17H, m), 1.8699-2.1238 (2H, m), 7.2888-8.1769 (7H, m) |
| Compound 11' | 324 | 1.5009-1.6206 (4H, t), 1.8125-1.8237 (4H, t), 1.9972-2.1835(1H,s), 3.8679(2H,s), 7.8943-8.4865(6H,m) |
| Compound 12' | 367 | 1.4805(12H,s), 1.67774(6H,s), 2.0163-2.3521(2H,s), 7.9165-8.1883(6H,m) |
| Compound13' | 477 | 1.3668(12H,s), 2.3679-2.3795(8H,t), 3.6775-3.8674(10H,m), 7.9992-8.1884(6H,m) |
| Compound 14' | 447 | 1.4003-1.4467(12H,m), 1.6775-1.7442(14H,m), 2.0354-2.3417(1H,s) 7.8766-8.1764(6H,m) |

Evaluation of Properties

By formulating representative photocurable resin compositions, respective application properties of the photoinitiators represented by the formula (I) of this invention were evaluated, including aspects such as photocuring property, odor property/mobility, and yellowing resistance and the like, and specific steps are as follows.

(1) Formulating a Photocurable Resin Composition Having the Following Composition:

| | |
|---|---|
| acrylate copolymer | 200 parts by mass |
| [benzyl methacrylate/methacrylic acid/ hydroxyethyl methacrylate (molar ratio: 70/10/20) copolymer (Mv: 10000)] | |
| dipentaerythritol hexaacrylate | 100 parts by mass |
| photoinitiator | 5 parts by mass |
| butanone (solvent) | 900 parts by mass |

In the composition described above, the photoinitiator was a compound of formula (I) of this invention or a photoinitiator known in the prior art (as a comparison).

(2) Test of Film-Forming Property

The composition described above was stirred under a yellow light lamp. Materials were taken on a PET template, a film was formed with roller coating and was dried at 90° C. for 2 min to obtain a coating film with a dry film thickness of 2 μm. It was cooled to room temperature, and the coating film was exposed by irradiating with a high-pressure mercury lamp (exposure machine model: RW-UV70201, exposure amount: 150 mJ/cm$^2$) to allow it to be cured to form a film.

The results of the test of film-forming property were shown in Table 2. Here, film colors and conditions of film surfaces were both directly observed with naked eye, and the odor was evaluated by a direct fan-smelling method. A darker film color indicates darker yellowing; A flatter surface indicates a better curing effect; and a lower odor indicates a smaller mobility.

TABLE 2

| Example/ Comparative Example | Photo- initiator | Film color | Film odor | Film surface |
|---|---|---|---|---|
| 15 | Compound 1' | Colorless | Ordorless | Flawless |
| 16 | Compound 2' | Colorless | Ordorless | Flawless |
| 17 | Compound 3' | Colorless | Ordorless | Flawless |
| 18 | Compound 6' | Colorless | Ordorless | Flawless |
| 19 | Compound 10' | Colorless | Ordorless | Flawless |
| Comparative Example 1 | Photoinitiator 907 | Yellow | Odorous | Flawless |
| Comparative Example 2 | Photoinitiator 1173 | Yellow | Ordorless | Flawless |
| Comparative Example 3 | Photoinitiator 184 | Colorless | Odorous | Flawless |
| Comparative Example 4 | Photoinitiator 369 | Colorless | Odorous | Flawless |

It can be seen from Table 2 that the film obtained after using the polyfunctional photoinitiator of this invention has a flawless surface and a good curing effect, the film colors are all colorless, and there is ordorless. Its curing effect is comparable as compared to conventional small molecular photoinitiators. However, it is superior to photoinitiators 907 and 1173 in terms of the alleviation of yellowing, and it is significantly superior to photoinitiators 907, 184, and 369 in terms of mobility.

In summary, the fluorene polyfunctional photoinitiator represented by formula (I) disclosed by this invention has excellent application properties. It has good photosensitive property and advantages of small odor, low mobility, good yellowing resistance, easy synthesis, low cost, and the like, and has very good application prospect in the field of photocuring.

Related Test of Composition

Photosensitive resin compositions of Examples 20-27 and Comparative Examples 5-8 were formulated according to the formulation listed in Table 3. Here, the structures of photoinitiators A1-A4 in Comparative Examples 5-8 were as shown below:

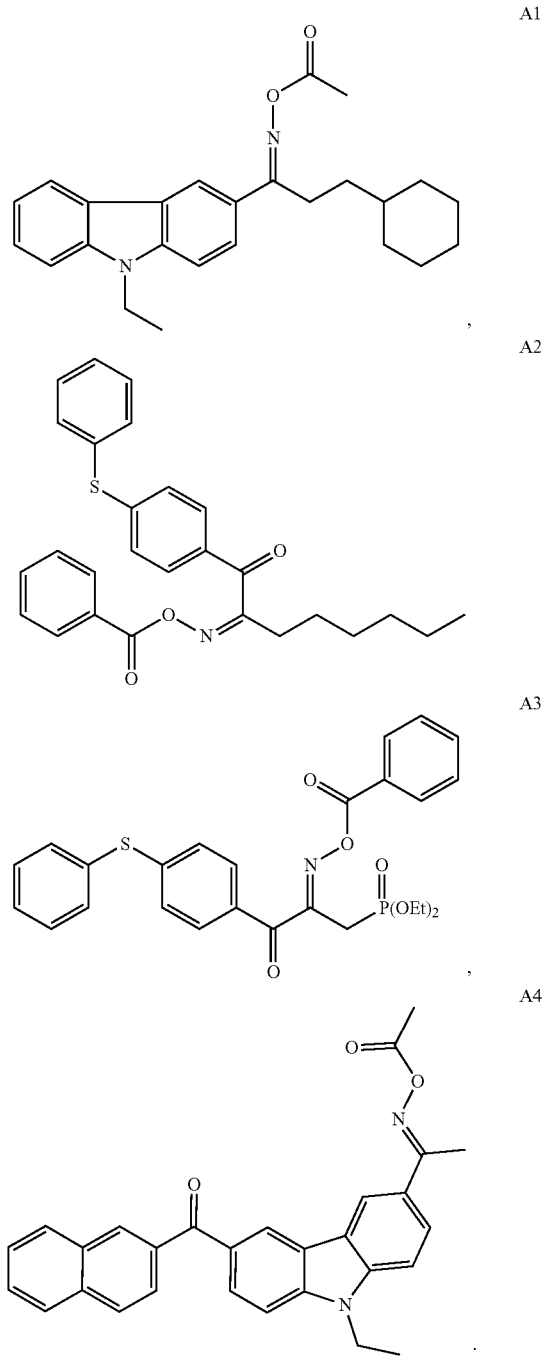

TABLE 3

| | (meth)acrylic acid/2-hydroxyethyl (meth)acylate/benzyl (meth)acrylate/polymethyl methacrylate (at a molar ratio of 70:10:20) macromer copolymer (Mv = 5000) | Dipentaelythritol hexamethacrylate | Photoinitiator (Types, Parts by mass) | Colorant (Types, Parts by mass) |
|---|---|---|---|---|
| Example 20 | 50 | 25 | Compound 2, 5 | Carbon black, 20 |
| Example 21 | 50 | 25 | Compound 5, 5 | Carbon black, 20 |
| Example 22 | 45 | 30 | Compound 8, 5 | Carbon black, 20 |
| Example 23 | 40 | 35 | Compound 9, 5 | Carbon black, 20 |
| Example 24 | 42 | 35 | Compound 10, 3 | Carbon black, 20 |
| Example 25 | 45 | 32 | Compound 13, 3 | C.I. Pigment blue-15:3, 20 |
| Example 26 | 50 | 25 | Compound 15, 5 | C.I. Pigment blue-15:3, 20 |
| Example 27 | 43 | 32 | Compound 28, 5 | C.I. Pigment blue-15:3, 20 |
| Comparative Example 5 | 42 | 35 | Compound A1, 3 | Carbon black, 20 |
| Comparative Example 6 | 50 | 25 | Compound A2, 5 | Carbon black, 20 |
| Comparative Example 7 | 45 | 25 | Compound A3, 5 | Carbon black, 20 |
| Comparative Example 8 | 43 | 32 | Compound A4, 5 | C.I. Pigment blue-15:3, 20 |

Note:
Those above are all parts by mass, and the compounds used by the photoinitiators in Examples 20 to 27 correspond to the compound listed in specific embodiments described above.

A photosensitive resin composition formulated according to the formulation shown in Table 3 was dissolved in 100 parts by mass of a solvent, propylene glycol monomethyl ether acetate (PGMEA), and uniformly mixed to form a liquid-state composition.

The liquid-state composition was coated on a glass substrate using a spin coater, and then the solvent was removed by drying at 100° C. for 5 min to form a coating film having a film thickness of 10 μm; and in order to obtain the coating film having the thickness described above, the process of coating may be completed by one time or by multiple times.

The substrate containing the coating film was cooled to room temperature, a mask plate was attached thereon, and exposure was performed on the coating film using an LED light source (UVATA LED UV curing radiation apparatus with a maximal radiation intensity of 400 mW/cm$^2$) through a seam of the mask plate under the irradiation of ultraviolet having a wavelength of 370-420 nm.

At a temperature of 25° C., 1% aqueous NaOH solution was used for development, ultra-pure pure water was used for washing, and air drying was performed.

Finally, baking was performed in an oven at 240° C. for 30 min to obtain a pattern transferred with the mask plate.

Evaluation of Properties

1. Evaluation of Exposure Sensitivity

The minimum exposure amount of the irradiated region having a residual film rate of 90% or more after development in the step of exposure was evaluated as the exposure demand. A smaller exposure demand indicates a higher sensitivity.

2. Evaluation of Developability and Pattern Integrity

The pattern on the substrate was observed using a scanning electron microscope (SEM) to evaluate the developability and the pattern integrity.

The developability was evaluated according to the following criteria: ○: No residue was observed in unexposed portions; ◉: A small amount of residue was observed in unexposed portions, but the residual amount is acceptable; ●: Significant residue was observed in unexposed portions.

The pattern integrity was evaluated according to the following criteria: Δ: Pattern defects were not observed; □: A few defects were observed in some portions of the pattern; ▲: A number of defects were significantly observed in the pattern.

3. Evaluation of Hardness

Evaluation was performed with reference to GB/T 6739-1996 "determination of film hardness by pencil test". Scratches of a paint film were observed using a coating film pencil scratch hardness instrument, and hardness of the pencil by which no scratch was seen was used as the pencil hardness of the coating film.

4. Evaluation of Adhesion

The adhesion of a coating film was evaluated by a crosscut test method with reference to GB9286-88 "Paints and Varnishes—Crosscut test for Films". According to the degree of damage, it is divided into 0-5 levels (6 levels in total), wherein level 0 is the best, and there is not any compartment which is peeled off the film surface; and level 5 is extremely bad, badly peeling occurring on the film surface.

Evaluation results were as shown in Table 4.

TABLE 4

| | Exposure demand mJ/cm$^2$ | Developability | Pattern integrity | Adhesion | Hardness |
|---|---|---|---|---|---|
| Example 20 | 68 | ○ | Δ | 0 | 5H |
| Example 21 | 69 | ○ | Δ | 0 | 5H |
| Example 22 | 65 | ○ | Δ | 0 | 5H |
| Example 23 | 69 | ○ | Δ | 0 | 5H |
| Example 24 | 68 | ○ | Δ | 0 | 5H |
| Example 25 | 66 | ○ | Δ | 0 | 5H |
| Example 26 | 70 | ○ | Δ | 0 | 5H |
| Example 27 | 70 | ○ | Δ | 0 | 5H |
| Comparative Example 5 | 102 | ● | ▲ | 4 | H |
| Comparative Example 6 | 98 | ◉ | □ | 2 | 2H |
| Comparative Example 7 | 85 | ◉ | □ | 3 | 2H |
| Comparative Example 8 | 78 | ◉ | □ | 2 | 4H |

It can be seen from the results of Table 4 that the color filter photoresists produced from the compositions of Examples 20-27 have good developability and pattern integrity and are also very excellent in terms of adhesion and hardness, and Comparative Examples 5-8 have significant deficiencies in these aspects. It is to be particularly noted that the exposure doses in Examples 20-27 all are no more than 70mJ/cm$^2$, which are far lower than those of Comparative Examples 5-8, exhibiting extremely excellent photosensitivity.

In summary, the photosensitive resin composition of this invention exhibits a very excellent application performance and has a wide prospect for application.

Those described above are merely preferred examples of this invention, and are not intended to limit this invention. With respect to a person skilled in the art, there may be various modifications and variations of this invention. All of modifications, equivalent replacements, improvements, and the like, which are within the spirit and the principle of this invention, should be encompassed in the scope protected by this invention.

What is claimed is:

1. A fluorene photoinitiator, having the structure as represented by the following formula (I):

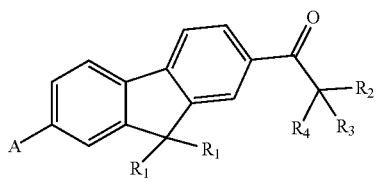

wherein, $R_1$ each independently represents hydrogen;

A represents hydrogen, a nitro group, halogen, or a —CO—$CR_2R_3R_4$ group;

$R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, as $C_4$-$C_{20}$ alkylcycloalkyl group, or a $C_6$-$C_{20}$ aryl group, and $R_2$ and $R_3$ may be linked to each other to form a ring and;

$R_4$ represents a photoactive group, which is a N-morpholinyl group.

2. The fluorene photoinitiator according to claim 1, wherein $R_2$ and $R_3$ each independently represent a $C_1$-$C_4$ linear or branched alkyl group or a $C_4$-$C_{10}$ cycloalkylalkyl group, or $R_2$ and $R_3$ are linked to each other to form a $C_3$-$C_{10}$ cycloalkyl group.

3. The fluorene photoinitiator according to claim 1, wherein $R_2$ and $R_3$ each independently represent a $C_1$-$C_4$ linear or branched alkyl group or a $C_4$-$C_8$ cycloalkylalkyl group, or $R_2$ and $R_3$ are linked to each other to form a $C_3$-$C_6$ cycloalkyl group.

4. The fluorene photoinitiator according to claim 1, wherein A represents hydrogen, a nitro group, or a —CO—$CR_2R_3R_4$ group.

* * * * *